US012605308B2

(12) United States Patent
Carle et al.

(10) Patent No.: US 12,605,308 B2
(45) Date of Patent: Apr. 21, 2026

(54) TOPICAL SKIN CARE FORMULATIONS COMPRISING PLANT EXTRACTS

(71) Applicant: MARY KAY INC., Addison, TX (US)

(72) Inventors: Tiffany Carle, Dallas, TX (US); David Gan, Southlake, TX (US); Michelle Hines, Hickory Creek, TX (US)

(73) Assignee: MARY KAY INC., Addison, TX (US)

( * ) Notice: Subject to any disclaimer, the term of this patent is extended or adjusted under 35 U.S.C. 154(b) by 63 days.

(21) Appl. No.: 18/381,436

(22) Filed: Oct. 18, 2023

(65) Prior Publication Data

US 2024/0042244 A1 Feb. 8, 2024

Related U.S. Application Data

(63) Continuation of application No. 17/980,256, filed on Nov. 3, 2022, now Pat. No. 11,865,373, which is a continuation of application No. 16/855,717, filed on Apr. 22, 2020, now Pat. No. 11,524,184, which is a continuation of application No. 16/233,503, filed on Dec. 27, 2018, now Pat. No. 10,668,009, which is a continuation of application No. 15/893,388, filed on Feb. 9, 2018, now Pat. No. 10,201,494, which is a continuation of application No. 15/214,182, filed on Jul. 19, 2016, now Pat. No. 9,913,798, which is a continuation of application No. 14/104,193, filed on Dec. 12, 2013, now Pat. No. 9,408,801, which is a continuation of application No. 13/888,068, filed on May 6, 2013, now Pat. No. 8,636,989, which is a continuation of application No. 13/453,690, filed on Apr. 23, 2012, now Pat. No. 8,444,959.

(60) Provisional application No. 61/477,812, filed on Apr. 21, 2011.

(51) Int. Cl.
| | |
|---|---|
| *A61K 36/14* | (2006.01) |
| *A61K 8/02* | (2006.01) |
| *A61K 8/04* | (2006.01) |
| *A61K 8/06* | (2006.01) |
| *A61K 8/9741* | (2017.01) |
| *A61K 8/9789* | (2017.01) |
| *A61K 8/9794* | (2017.01) |
| *A61K 36/185* | (2006.01) |
| *A61K 36/48* | (2006.01) |
| *A61K 36/74* | (2006.01) |
| *A61Q 17/04* | (2006.01) |
| *A61Q 19/00* | (2006.01) |
| *A61Q 19/02* | (2006.01) |
| *A61Q 19/08* | (2006.01) |

(52) U.S. Cl.
CPC ............ *A61Q 17/04* (2013.01); *A61K 8/0212* (2013.01); *A61K 8/022* (2013.01); *A61K 8/042* (2013.01); *A61K 8/062* (2013.01); *A61K 8/9741* (2017.08); *A61K 8/9789* (2017.08); *A61K 8/9794* (2017.08); *A61K 36/14* (2013.01); *A61K 36/185* (2013.01); *A61K 36/48* (2013.01); *A61K 36/577* (2024.05); *A61K 36/74* (2013.01); *A61Q 19/00* (2013.01); *A61Q 19/008* (2013.01); *A61Q 19/02* (2013.01); *A61Q 19/08* (2013.01); *A61K 2800/31* (2013.01); *A61K 2800/782* (2013.01)

(58) Field of Classification Search
CPC ...................................................... A61K 8/022
See application file for complete search history.

(56) References Cited

U.S. PATENT DOCUMENTS

| | | | |
|---|---|---|---|
| 5,705,170 | A | 1/1998 | Kong et al. |
| 7,759,393 | B2 | 7/2010 | Joerger et al. |
| 2006/0134095 | A1 | 6/2006 | Ito et al. |
| 2007/0122492 | A1 | 5/2007 | Behr et al. |
| 2008/0044502 | A1 | 2/2008 | Wirth et al. |
| 2008/0227842 | A1 | 9/2008 | Krautler et al. |
| 2009/0068255 | A1 | 3/2009 | Yu et al. |
| 2009/0149420 | A1 | 6/2009 | Raederstorff et al. |
| 2010/0291049 | A1 | 11/2010 | Izawa et al. |
| 2010/0331274 | A1 | 12/2010 | Gupta |
| 2011/0151031 | A1 | 6/2011 | Futamura |
| 2012/0003332 | A1 | 1/2012 | Zheng et al. |

FOREIGN PATENT DOCUMENTS

| | | | |
|---|---|---|---|
| CN | 101686728 | | 3/2010 |
| JP | 2001-187725 | | 7/2001 |
| JP | 2003-113064 | | 4/2003 |
| JP | 2008-247854 | | 10/2008 |
| JP | 2009108025 | * | 5/2009 |
| KR | 980008212 | | 4/1998 |
| KR | 20030020289 | | 3/2003 |
| KR | 2003-0061847 | | 7/2003 |

(Continued)

OTHER PUBLICATIONS

Ghimire et al. (A comprehensive review on phytochemical, pharmacognostical properties and pharmacological activities of *Ficus lacor* L. (Moraceae)). (Year: 2020).*

(Continued)

*Primary Examiner* — Sarah Alawadi

(74) *Attorney, Agent, or Firm* — NORTON ROSE FULBRIGHT US LLP

(57) ABSTRACT

A method for treating skin of a person in need thereof is disclosed. The method includes topically applying to the skin of the person a composition comprising an effective amount of an aqueous, alcoholic, or aqueous-alcoholic extract from *Ficus lacor*, wherein the extract from *Ficus lacor* reduces oxidation in the skin or reduces MMP-1 activity in the skin.

22 Claims, 1 Drawing Sheet

(56) References Cited

FOREIGN PATENT DOCUMENTS

| | | |
|---|---|---|
| KR | 20080094458 | 10/2008 |
| KR | 20180083353 | 7/2018 |
| KR | 102121704 | 6/2020 |
| KR | 20200083673 | 7/2020 |
| KR | 102389984 | 4/2022 |
| KR | 102545052 | 6/2023 |
| WO | WO200511590 | * 12/2005 |
| WO | WO 2010111745 | 4/2010 |

OTHER PUBLICATIONS

Sirisha et al. Antioxidant Properties of Ficus Species—A review. (Year: 2010).*

"Isolectotype of Cudrania pubescens Trécul [family Moraceae]" *Global Plants*, 2010, JSTOR, https://plants.jstor.org/stable/10.5555/al.ap.specimen.p00745451?.

"Natural Hair Color Henna & Amla" Khadi, https://www/khadl.de/ed/hair/natural-hair-color/khadi-natural-hair-color-henna-amis.html, retrieved from the internet on Jun. 10, 2021.

Brazier, "What to Know about Wrinkles", 2020.

Chae et al., "Antioxidant Activity of Jionoside D from *Clerodendron trichotomum*", *Biol Pharm. Bull*, 27(10):1504-1508, (2004).

Chae et al., "Antioxidant Activity of Isoacteoside from *Clerodendron trichotomum*", *J Toxicol Environ Health A*, 68(5):389-400, (2005).

Chae et al., "Trichotomoside: A New Antioxidative Phenylpropanoid Glycoside from *Clerodendron trichotomum*," *Chemistry and Biodiversity*, 3(1):41-48, (2006).

International Search Report and Written Opinion issued in PCT Application No. PCT/US2012/034673, dated Nov. 26, 2012.

Nischik et al., "Analysis of Skin Erythema Using True-Color Images" *IEEE Transactions on Medical Imaging* 1997, 16(6), pp. 711-716.

Office Action issued in Chinese Application No. 201280022458.6, dated Dec. 5, 2014.

Office Action issued in Corresponding Canadian Application No. 3,057,795, dated Aug. 2, 2023.

Office Action issued in Corresponding Korean Application no. 10-2022-7012853, dated Jul. 26, 2022 (English Translation provided).

Palmer et al., "Oxidative damage, skin aging, antioxidants and a novel antioxidant rating system," *Journal of Drugs in Dermatology*, 9(1):11-15, (2010).

Personal care, "Shea Butter with Improved Mositurisation Properties" (2009).

Sander et al., "Photoaging is Associated with Protein Oxidation in Human Skin In Vivo", *Journal of Investigative Dermatology*, 118(4):618-625, (2002).

Yoon et al., "Antioxidant Activity and Whitening Effects of Acteoside and Isoacteoside", *The Pharmaceutical Society of Korea*, 53(1):1-5, (2009). (English Abstract).

Lertsatitthanakorn, P et al., "In vitro bioactivities of essential oils used for acne control" *The International Journal of Aromatherapy*, 16, 2006, pp. 43-49.

Office Action issued in Corresponding Korean Application No. 10-2023-7020016, dated Dec. 1, 2023 (English Translation provided).

* cited by examiner

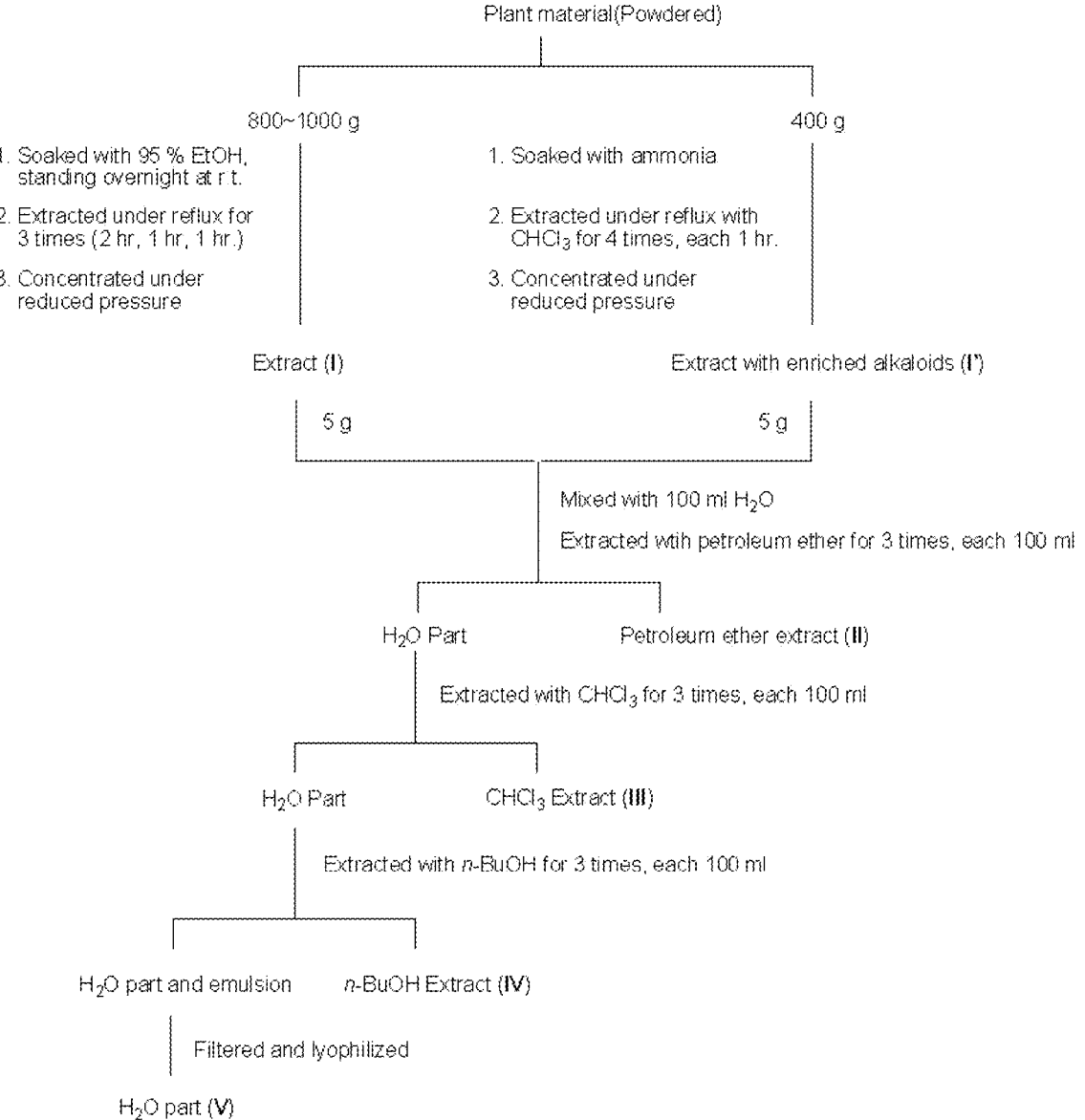

TOPICAL SKIN CARE FORMULATIONS COMPRISING PLANT EXTRACTS

CROSS REFERENCE TO RELATED APPLICATIONS

This application is a continuation of U.S. application Ser. No. 17/980,256 filed Nov. 3, 2022, which is a continuation of U.S. application Ser. No. 16/855,717 filed Apr. 22, 2020 (now U.S. Pat. No. 11,524,184), which is a continuation of U.S. application Ser. No. 16/233,503 filed Dec. 27, 2018 (now U.S. Pat. No. 10,668,009), which is a continuation of U.S. application Ser. No. 15/893,388 filed Feb. 9, 2018 (now U.S. Pat. No. 10,201,494), which is a continuation of U.S. application Ser. No. 15/214,182 filed Jul. 19, 2016 (now U.S. Pat. No. 9,913,798), which is a continuation of U.S. application Ser. No. 14/104,193 filed Dec. 12, 2013 (now U.S. Pat. No. 9,408,801), which is a continuation of U.S. application Ser. No. 13/888,068 filed May 6, 2013 (now U.S. Pat. No. 8,636,989), which is a continuation of U.S. application Ser. No. 13/453,690 filed Apr. 23, 2012 (now U.S. Pat. No. 8,444,959), which claims the benefit of U.S. Provisional Application No. 61/477,812 filed Apr. 21, 2011. The contents of each referenced application are incorporated into the present application by reference.

BACKGROUND OF THE INVENTION

A. Field of the Invention

The present invention relates generally to compositions that include one or any combination of plant extracts to treat a variety of skin conditions. The extracts can be included in topical skin compositions, edible compositions, injectable compositions, oral compositions, hair care compositions, etc.

B. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods.

SUMMARY OF THE INVENTION

The inventors discovered that particular sets of ingredients can be used to treat certain skin conditions ranging from fine lines or wrinkles, oily skin or excessive sebum production, and skin having dark spots (e.g., liver spots, age spots, etc.), melasma, hyperpigmentation, and uneven skin tone.

In one instance, for example, there is disclosed a topical skin composition comprising a first MMP-1 inhibitor, wherein said first inhibitor can be an extract from *Burretiodendron hsienmu*, a second MMP-1 inhibitor, wherein said second inhibitor can be an extract from *Bauhinia brachycarpa* var. *cavaleriei*, and a third MMP-1 inhibitor, wherein said third inhibitor can be an extract from *Tetracentron sinense*. The composition can take the form of an emulsion (e.g., w/o, o/w, w/si, si/w, w/o/w, w/si/w, o/w/o, si/w/si) a cream, a lotion, a solution, an anhydrous stick, a serum, etc. The composition can include from about 0.001% to about 5% by weight of said extract from *Burretiodendron hsienmu*, from about 0.001% to about 5% by weight of said extract from *Bauhinia brachycarpa* var. *cavaleriei*, and from about 0.001% to about 5% by weight of said extract from *Tetracentron sinense* (ranges inside and out side of the stated range is also contemplated, e.g., 0.0001%, 6%, 7%, 8%, 9%, 10%, 15%, 20%, and more). The composition can further include a moisturization agent, an antioxidant, a structuring or thickening agent, and/or an emulsifier (examples of each of these ingredients is provided below). The composition can further include a silicone containing compound and/or a sunscreen agent (examples of these ingredients are also provided below). The extracts can be aqueous extracts, alcoholic extracts, glycolic extracts, or oil extracts. In particular instances, the extracts are aqueous extracts. The extracts can each be obtained from the whole plant of *Burretiodendron hsienmu, Bauhinia brachycarpa* var. *cavaleriei*, and *Tetracentron sinense*, or from any part of the plant thereof (e.g., root, stem, leaf, flower, seed) at the exclusion of other parts of the plant. In particular instances, the extracts are aqueous extracts from the whole plants, respectively. The composition can be formulated as a cleanser product, a toner product, a moisturizer product, or a mask product. Additionally, each of the MMP-1 inhibitors can also have further functionalities that can be beneficial to skin. For instance, the first MMP-1 inhibitor can also be an antioxidant, a lipoxygenase inhibitor, and a tyrosinase inhibitor. The second MMP-1 inhibitor can also be an antioxidant and a lipoxygenase inhibitor. The third MMP-1 inhibitor can also be an antioxidant. Further, the combined extracts can be used to treat a variety of skin conditions by applying a composition having said extracts to skin in need of such treatment. As indicated above, the composition can be effective in inhibiting MMP-1 activity in skin, which can aid in reducing the appearance of fine lines and wrinkles, sagging skin, loose skin, and/or skin that has an overall aged appearance. The composition can also inhibit lipoxygenase activity, which can further aid in the skin treatment process while having an added benefit of reducing sebum production in skin cells, thereby treating the appearance of oily skin. The composition can also inhibit tyrosinase activity, which is a key enzyme in the pathway for producing melanin. This can be used to reduce the appearance of hyperpigmented skin, sun spots, aged spots, liver spots, melasma, and/or uneven skin tone. Further, the composition can be used to reduce oxidative damage in skin cells, which can provide both a treatment and protection function from reactive oxygen species and the like. Also, the composition can be a leave-on or rinse of composition.

In another instance, the inventors discovered that a combination of extracts from *Circidiphyllum japonicum, Bauhinia glauca*, and *Rhododendron siderophyllum* can be used to inhibit lipoxygenase activity in skin. In this regard, there is disclosed a topical skin composition comprising a first lipoxygenase inhibitor, wherein said first inhibitor can be an extract from *Circidiphyllum japonicum*, a second lipoxygenase inhibitor, wherein said second inhibitor can be an extract from *Bauhinia glauca*, and a third lipoxygenase inhibitor, wherein said third inhibitor can be an extract from *Rhododendron siderophyllum*. The composition can take the form of an emulsion (e.g., w/o, o/w, w/si, si/w, w/o/w, w/si/w, o/w/o, si/w/si) a cream, a lotion, a solution, an anhydrous stick, a serum, etc. The composition can include from about 0.001% to about 5% by weight of said extract from *Circidiphyllum japonicum*, from about 0.001% to about 5% by weight of said extract from *Bauhinia glauca*, and from about 0.001% to about 5% by weight of said extract from *Rhododendron siderophyllum* (ranges inside and out side of the stated range is also contemplated, e.g., 0.0001%, 6%, 7%, 8%, 9%, 10%, 15%, 20%, and more). The composition can further include a moisturization agent, an antioxidant, a structuring or thickening agent, and/or an emulsifier (examples of each of these ingredients is provided below). The composition can further include a silicone containing compound and/or a sunscreen agent (examples of these ingredients are also provided below). The extracts can be aqueous extracts, alcoholic extracts, glycolic extracts, or oil extracts. In particular instances, the extracts are aqueous extracts. The extracts can each be obtained from the whole plant of *Circidiphyllum japonicum, Bauhinia glauca*, and *Rhododendron siderophyllum*, or from any part of the plant thereof (e.g., root, stem, leaf, flower, seed) at the exclusion of other parts of the plant. In particular instances, the extracts are aqueous extracts from the whole plants, respectively. The composition can be formulated as a cleanser product, a toner product, a moisturizer product, or a mask product. Additionally, each of the lipoxygenase inhibitors can also have further functionalities that can be beneficial to skin. For instance, the first lipoxygenase inhibitor can also be an antioxidant and a MMP-1 inhibitor. The second lipoxygenase inhibitor can be an antioxidant, a MMP-1 inhibitor, and a tyrosinase inhibitor. The third lipoxygenase inhibitor can be an antioxidant and a MMP-1 inhibitor. Further, the combined extracts can be used to treat a variety of skin conditions by applying a composition having said extracts to skin in need of such treatment. As indicated above, the composition can be effective in inhibiting lipoxygenase activity, which can further aid in the skin treatment process while having an added benefit of reducing sebum production in skin cells, thereby treating the appearance of oily skin. The composition can also inhibit MMP-1 activity in skin, which can aid in reducing the appearance of fine lines and wrinkles, sagging skin, loose skin, and/or skin that has an overall aged appearance. The composition can also inhibit tyrosinase activity, which is a key enzyme in the pathway for producing melanin. This can be used to reduce the appearance of hyperpigmented skin, sun spots, aged spots, liver spots, melasma, and/or uneven skin tone. Further, the composition can be used to reduce oxidative damage in skin cells, which can provide both a treatment and protection function from reactive oxygen species and the like. Also, the composition can be a leave-on or rinse of composition.

In another instance, the inventors discovered that a combination of extracts from *Burretiodendron hsienmu, Bauhinia glauca*, and *Wendlandia uvariifolia* can be used to inhibit tyrosinase activity in skin. In this regard, there is disclosed a topical skin composition comprising a first tyrosinase inhibitor, wherein said first inhibitor can be an extract from *Burretiodendron hsienmu*, a second tyrosinase inhibitor, wherein said second inhibitor can be an extract from *Bauhinia glauca*, and a third tyrosinase inhibitor, wherein said third inhibitor can be an extract from *Wendlandia uvariifolia*. The composition can take the form of an emulsion (e.g., w/o, o/w, w/si, si/w, w/o/w, w/si/w, o/w/o, si/w/si) a cream, a lotion, a solution, an anhydrous stick, a serum, etc. The composition can include from about 0.001% to about 5% by weight of said extract from *Burretiodendron hsienmu*, from about 0.001% to about 5% by weight of said extract from *Bauhinia glauca*, and from about 0.001% to about 5% by weight of said extract from *Wendlandia uvariifolia* (ranges inside and out side of the stated range is also contemplated, e.g., 0.0001%, 6%, 7%, 8%, 9%, 10%, 15%, 20%, and more). The composition can further include a moisturization agent, an antioxidant, a structuring or thickening agent, and/or an emulsifier (examples of each of these ingredients is provided below). The composition can further include a silicone containing compound and/or a sunscreen agent (examples of these ingredients are also provided below). The extracts can be aqueous extracts, alcoholic extracts, glycolic extracts, or oil extracts. In particular instances, the extracts are aqueous extracts. The extracts can each be obtained from the whole plant of *Burretiodendron hsienmu, Bauhinia glauca*, and *Wendlandia uvariifolia*, or from any part of the plant thereof (e.g., root, stem, leaf, flower, seed) at the exclusion of other parts of the plant. In particular instances, the extracts are aqueous extracts from the whole plants, respectively. The composition can be formulated as a cleanser product, a toner product, a moisturizer product, or a mask product. Additionally, each of the tyrosinase inhibitors can also have further functionalities that can be beneficial to skin. For instance, the first tyrosinase inhibitor can also be an antioxidant, a MMP-1 inhibitor, and a lipoxygenase inhibitor. The second tyrosinase inhibitor can also be an antioxidant, a MMP-1 inhibitor, and a lipoxygenase inhibitor. The third tyrosinase inhibitor can also be an antioxidant and a MMP-1 inhibitor. Further, the combined extracts can be used to treat a variety of skin conditions by applying a composition having said extracts to skin in need of such treatment. As indicated above, the composition can be effective in inhibiting tyrosinase activity, which is a key enzyme in the pathway for producing melanin. This can be used to reduce the appearance of hyperpigmented skin, sun spots, aged spots, liver spots, melasma, and/or uneven skin tone. The composition can also be used to inhibit lipoxygenase activity, which can further aid in the skin treatment process while having an added benefit of reducing sebum production in skin cells, thereby treating the appearance of oily skin. The composition can also inhibit MMP-1 activity in skin, which can aid in reducing the appearance of fine lines and wrinkles, sagging skin, loose skin, and/or skin that has an overall aged appearance. Further, the composition can be used to reduce oxidative damage in skin cells, which can provide both a treatment and protection function from reactive oxygen species and the like. Also, the composition can be a leave-on or rinse of composition.

In addition to the above combinations of ingredients, the inventors also discovered that a wide variety of individual plants and extracts thereof have therapeutic benefits. These plants and extracts thereof are from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Caja-* nus cajan, Wendlandia uvariifolia, Siegesbeckia glabrescens, Azolla imbricate, Juncus bufonius, Poikilospermum suaveolens, Clerodendrum trichotomum var. fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus, and/or Solanum carolinense. In particular aspects, compositions of the present invention can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The extracts can be included in compositions such as topical skin compositions, edible compositions, injectable compositions, oral compositions, pharmaceutical compositions, hair care compositions, etc. The composition can include 0.01% to 20% by weight of said plant, plant part, and/or extract thereof (or 0.1, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80, 90, 99%, or more or any integer or range therein).

In particular aspects, the composition is formulated as topical skin composition. The composition can have a dermatologically acceptable vehicle or carrier for the plant, plant part, or extract thereof. The composition can further include a moisturizing agent or a humectant, a surfactant, a silicone containing compounds, a UV agent, an oil, and/or other ingredients identified in this specification or those known in the art. The composition can be a lotion, cream, gel, serum, emulsion (e.g., oil-in-water, water-in-oil, silicone-in-water, water-in-silicone, water-in-oil-in-water, oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or over night or throughout the day). In more particular instances, a leave-on composition remains on the skin for at least 1 hour after application. Alternatively, a rinse-off composition can be a product that is intended to be applied to the skin and then removed or rinsed from the skin (e.g., with water) within a period of time such as less than 5, 4, 3, 2, or 1 minute(s). An example of a rinse of composition can be a skin cleanser, shampoo, conditioner, or soap. An example of a leave-on composition can be a skin moisturizer, sunscreen, mask, overnight cream, or a day cream.

The compositions of the present invention can also be modified to have a desired oxygen radical absorbance capacity (ORAC) value. In certain non-limiting aspects, the compositions of the present invention or the plant, plant parts, or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In another embodiment, there is disclosed a topical skin care composition that includes an one of or combination of the aforementioned plants, plant parts, and/or extracts thereof in combination with any one of, any combination of, or all of the following ingredients: water; glycerin; butylene glycol; propylene glycol; phenoxyethanol; a chelating agent (e.g., EDTA, disodium EDTA, trisodium EDTA, EGTA, disodium EGTA, trisodium EGTA, citric acid, phosphoric acid, succinic acid, etc.); steareth-20; chlorhexidine diglunonate; potassium sorbate; and/or a preservative (e.g., methylparaben, propylparaben, butylparaben, ethylparaben, isobutylparaben, etc.). In particular aspects, the composition can further include any one of, any combination of, or all of the following additional ingredients: alcohol; denatured alcohol; glyceryl stearate; dimethicone; PEG-100 stearate; capryl glycol; triethanolamine; maltodextrin; sorbic acid; ethylene brassylate; methyl linalool; isobutyl methyl tetra-hydropyranol; ethylhexylglycerin; and/or hexylene glycol. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water.

In another embodiment, there is disclosed a topical skin care composition that includes an one of or combination of the aforementioned plants, plant parts, and/or extracts thereof in combination with any one of, any combination of, or all of the following ingredients: water; dimethicone; triethanolamine; phenonip; betaine; a chelating agent (e.g., EDTA, disodium EDTA, trisodium EDTA, EGTA, disodium EGTA, trisodium EGTA, citric acid, phosphoric acid, suc-cinic acid, etc.); tocopheryl acetate; and/or prodew 400. In particular aspects, the composition can further include any one of, any combination of, or all of the following additional ingredients: propylene glycol; isododecane; polyacrylam-ide/C13-C14 isoparaffin/laureth 7 mixture; PEG-12 dime-thicone; and/or ethylhexyl palmitate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water.

In another embodiment, there is disclosed a topical skin care composition that includes an one of or combination of the aforementioned plants, plant parts, and/or extracts thereof in combination with any one of, any combination of, or all of the following ingredients: water; glycerin; penty-lene glycol; capryl glycol; disodium EDTA; capric/caprylic triglyceride; shea butter; squalane; cetyl alcohol; dimethi-cone; ceramide II; stearic acid; a mixture of glyceryl stearate and PEG 100 stearate; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concen-tration of water can be at least 35% to 80% by weight of water. The ratio of water to glycerin can be from about 7:1 to 9:1 based on the total weight of the composition. The ratio of glycerin to pentylene glycol can be from about 1:1 to about 2:1 based on the total weight of the composition.

In another embodiment, there is disclosed a topical skin care composition that includes any one of or combination of the aforementioned plants, plant parts, and/or extracts thereof in combination with any one of, any combination of, or all of the following ingredients: water; glycerin; capryl glycol; capryl glycol; disodium EDTA; petrolatum; squalane; cetyl alcohol; a mixture of glyceryl stearate and PEG 100 stearate; dimethicone; or a mixture of acrylamide/ acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 12:1 to 16:1 based on the total weight of the composition. The ratio of glycerin to pentylene glycol can be from about 0.5:1 to about 1.5:1 based on the total weight of the composition.

In another embodiment, there is disclosed a topical skin care composition that includes any one of or combination of the aforementioned plants, plant parts, and/or extracts thereof in combination with any one of, any combination of, or all of the following ingredients: water; xanthan gum; disodium EDTA; pentylene glycol; capryl glycol; acrylate C10-30 acrylate cross polymer; triethanolamine; PVP/hexa-decene copolymer; C12-15 alkyl benzoate; sorbitan isoste-arate; or a sunscreen agent. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to C12-15 alkyl benzoate can be from about 2:1 to 3:1 based on the total weight of the composition. The ratio of water to pentylene glycol can be from about 9:1 to about 11:1 based on the total weight of the composition.

In another embodiment, there is disclosed a topical skin care composition that includes any one of or combination of the aforementioned plants, plant parts, and/or extracts thereof in combination with any one of, any combination of, or all of the following ingredients: water; disodium EDTA; citric acid; pentylene glycol; capryl glycol; sodium coco-amphodiacetate; or sodium methyl cocoyl taurate. The con-centrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to pentylene glycol can be from about 12:1 to 14:1 based on the total weight of the composition. The ratio of water to sodium cocoamphodiacetate can be from about 8:1 to about 11:1 based on the total weight of the compo-sition. The ratio of water to sodium methyl cocoyl taurate can be from about 2:1 to about 4:1 based on the total weight of the composition. The ratio of sodium methyl cocoyl taurate to sodium cocoamphodiacetate can be from about 2:1 to about 4:1 based on the total weight of the composition.

Also disclosed is an extract from *Phaseolus vulgaris, Citris sinensis, Wedelia trilobata, Burretiodendron hsienmu, Bauhinia brachycarpa* var. *cavaleriei, Cystacanthus panicu-latus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Caja-nus cajan, Wendlandia uvariifolia, Siegesbeckia glabre-scens, Azolla imbricate, Juncus bufonius, Poikilospermum suaveolens, Clerodendrum trichotomum* var. *fargesii, Porandra ramosa, Annona glabra, Sterculia pexa, Phoebe*

*puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense.* The extract can be from the whole plant or part of the plant (e.g., root, bark, sap, stem, leaf, flower, seed, leaf, stem, root, flower, seed, sap, bark, etc.), or mixtures from different parts of the plant. The extract can be an aqueous extract or a non-aqueous extract. The extract can be extracted with alcohol (e.g., methanol, ethanol propanol, butanol, etc.), glycols, oils, water, etc. The extracts can be included in a composition. The composition can include 0.01% to 20% by weight of said plant, plant part, and/or extract thereof (or 0.1, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80, 90, 99%, or more or any integer or range therein). The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, or extracts thereof. The composition can be an edible composition. The composition can take the form of a pill, liquid gel cap, tablet, or powder. The composition can be an injectable solution (e.g., for intravenous delivery). The composition can be in the form of a neutraceutical. The composition can be a topical skin composition. The composition can be in aerosolized form. The extract can be an aqueous or a non-aqueous extract. The aqueous extract can include an alcohol, a glycol, water and/or water. Non-aqueous extract can include a fat or an oil.

One aspect of the present invention concerns a method of treating or preventing a skin condition comprising topically applying any one of the compositions disclosed in this specification to skin having a skin condition. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense.* The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can include a dermatologically acceptable vehicle. Non-limiting examples of skin conditions that can be treated and/or prevented with the compositions of the present invention include dry skin, itchy skin, flaky skin, inflamed skin, erythemic skin, pain associated with erythemic skin, sensitive skin, pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, postules, nodules, whiteheads, blackheads, impetigo, erysipelas, erythrasma, eczema, sun burns, burned skin, open wounds, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids; inhibit melanin production in melanocytes; reduce or prevent oxidative damage to skin (including reducing the amount of lipid peroxides and/or protein oxidation in the skin).

In yet another embodiment, the extracts disclosed throughout this specification can be used treat skin conditions or diseases associated with oxidation of skin cells (e.g., extracts that have antioxidative properties), tyrosinase activity (e.g., extracts that have the ability to modify or otherwise inhibit tyrosinase activity in skin cells), lipoxygenase activity (e.g., extracts that have the ability to modify or otherwise inhibit lipoxygenase activity), and/or MMP-1 activity (e.g., extracts that have the ability to modify or otherwise inhibit MMP-1 activity). The data in the Examples and the information provided in the Detailed Description concerning the extracts provide information on the antioxidant, tyrosinase inhibition, lipoxygenase inhibition, and MMP-1 inhibition abilities of said extracts. In particular embodiments, extracts that have antioxidant properties can be used to treat, prevent, or reduce oxidative damage to skin cells from external environmental factors (e.g., pollution, sun, chemicals, etc.). Extracts having tyrosinase inhibiton properties can be used to reduce or otherwise prevent tyrosinase production or activity in skin cells, which can be used to treat hyperpigmented skin, uneven skin, melasmic skin, dark spots, aged spots, sun spots, blotchy skin, etc. Extracts having MMP-1 inhibition properties can be used to maintain or prevent collagen breakdown in skin cells and can be used to treat or prevent fine lines and wrinkles, sagging skin, loose skin, etc.

In one embodiment of the present invention there is disclosed a method of reducing the appearance of symptoms associated with erythema (e.g., erythemic skin, sensitive skin, inflamed skin) comprising topically applying any one of the compositions of the present invention to skin in need thereof. Erythema can be caused by skin sunburn, electrical treatments of skin, skin burns, contact allergies, systemic allergies, skin toxicity, exercise, insect stings, bacterial infection, viral infection, fungal infection, protozoa infection, massage, windburn, etc. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

In still another aspect of the present invention there is disclosed a method of treating dry, flaky, or itchy skin or reducing the appearance of uneven skin tone comprising topically applying any one of the compositions disclosed in this specification to dry, flaky, or itchy skin or to skin having an uneven skin tone. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala mada-*

*gascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

Also disclosed is a method of reducing the appearance of fine lines or wrinkles comprising topically applying any one of the compositions disclosed in this specification to skin having fine lines or wrinkles. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc.

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense.* The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can be formulated as a topical composition, an ingestible composition, an injectable composition, an aerosolized composition, etc. Non-limiting examples of diseases that can be treated or prevented with such compositions include AIDS, autoimmune diseases (e.g., rheumatoid arthritis, multiple sclerosis, diabetes-insulin-dependent and non-independent, systemic lupus erythematosus and Graves disease), cancer (e.g., malignant, benign, metastatic, precancer), cardiovascular diseases (e.g., heart disease or coronary artery disease, stroke-ischemic and hemorrhagic, and rheumatic heart disease), diseases of the nervous system, and infection by pathogenic microorganisms (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis), inflammation (e.g., allergy, asthma), prion diseases (e.g., CID, kuru, GSS, FFI), obesity, etc.

In yet another aspect of the present invention there is disclosed a method of treating or preventing a wide variety of diseases comprising administering to a patient in need of treatment any one of the compositions of the present invention. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe*

*puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense.* The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can be formulated as a topical composition, an ingestible composition, an injectable composition, an aerosolized composition, etc. Non-limiting examples of diseases that can be treated or prevented with such compositions include AIDS, autoimmune diseases (e.g., rheumatoid arthritis, multiple sclerosis, diabetes-insulin-dependent and non-independent, systemic lupus erythematosus and Graves disease), cancer (e.g., malignant, benign, metastatic, precancer), cardiovascular diseases (e.g., heart disease or coronary artery disease, stroke-ischemic and hemorrhagic, and rheumatic heart disease), diseases of the nervous system, and infection by pathogenic microorganisms (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis), inflammation (e.g., allergy, asthma), prion diseases (e.g., CID, kuru, GSS, FFI), obesity, etc.

Also disclosed is a method thickening hair or treating or preventing hair loss on the scalp (e.g., male-pattern baldness, female-pattern baldness, cicatricial alopecia, alopecia areata telogen effluvium, traction alopecia, anagen effluvium), eyebrows, or eyelashes comprising administering to a patient in need of any such treatment any one of the compositions of the present invention. As noted throughout, the composition can include a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiti-*

15                                                                16

*cus*, and/or *Solanum carolinense*. The composition can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of said plants, plant parts, and/or extracts thereof. The plant part can be the whole plant or part of the plant (e.g., root, bark, sap, stem, leaf, flower, seed, leaf, stem, root, flower, seed, sap, bark, etc.). The extract can be from the whole plant or part of the plant (e.g., root, bark, sap, stem, leaf, flower, seed, leaf, stem, root, flower, seed, sap, bark, etc.). The extract can be an aqueous extract or a non-aqueous extract. The extract can be extracted with alcohol (e.g., methanol, ethanol propanol, butanol, etc.), glycols, oils, water, etc. The composition can be formulated as a topical composition, an ingestible composition, an injectable composition, an aerosolized composition, a foam based composition etc. An assay that can be used to test a composition's ability to thicken hair or treat or prevent hair loss is to apply test composition to a targeted area and measure new hair growth or rate of hair loss when compared with a controlled area that is not receiving the test composition. The method can also include combining any one of the compositions of the present invention with known hair loss or hair thickening treatments (e.g., 5-α reductase inhibitors (e.g., finasteride, dutasteride, saw palmetto extract etc.), vasodilators (e.g., minoxidil), ketoconazole, hair transplantation procedures, hair multiplication procedures, laser therapy, caffeine, etc.).

In one particular non-limiting embodiment, the extract or extracts used in any one of the treatment methods described above and throughout this specification and claims is prepared in accordance with the procedures described in The FIGURE. The contents of The FIGURE are incorporated by reference.

Multipurpose compositions are also contemplated. For instance, compositions that can have antioxidant properties, inhibit or reduce lipoxygenase activity, inhibit or reduce tyrosinase activity, and/or inhibition or reduce MMP-1 activity, or any 2, 3, 4, or all of such properties is contemplated. Such compositions can be prepared in view of the information provided in the Detailed Description and Examples sections of this specification, which explains the abilities of the extracts.

The compositions of the present invention can also take the form of topically spreadable compositions, sprayable compositions, aerosolized compositions, injectable compositions, edible compositions, compositions in tablet, gel cap, or pill form. The extract used within the compositions and methods of the present invention can be aqueous extracts, alcoholic extracts, glycolic extracts, oil extracts, or any combination thereof. The compositions can be in powdered form, liquid form, or aerosolized form. The extracts can prepared in accordance with the process described in The FIGURE.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is also contemplated that compositions of the present invention can be included into food-based products (e.g., beverages, fortified water, energy drinks, nutritional drinks, solid foods, vitamins, supplements, etc.) and pharmaceutical products (e.g., pills, tablets, gel capsules, injectable solutions, drugs, etc.). "Supplements" can include vitamins, minerals, herbs or other botanicals, amino acids, enzymes and metabolites. Such supplements are suitable for oral consumption and can be administered orally.

The compositions and methods for their use can "comprise," "consist essentially of," or "consist of" any of the ingredients disclosed throughout the specification. "Consisting essentially of" means that inclusion of additional ingredients in the compositions do not materially affect the beneficial properties of the compositions. For instance, if a composition "consists essentially of" an MMP-1 inhibitor, a lipoxygenase inhibitor, and/or a tyrosinase inhibitor, then said composition excludes any ingredients that would materially affect the beneficial properties of said inhibitor. Similarly, if a composition "consists essentially of" an antioxidant, then said composition excludes any ingredients that would materially affect the beneficial properties of said antioxidant.

Further, the contents of U.S. application Ser. No. 12/869, 352, filed Aug. 26, 2010, International Application No. PCT/US/10/46791, filed Aug. 26, 2010, and U.S. provisional Application No. 61/237,087, filed Aug. 26, 2009 are incorporated by reference into the present application.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

The FIGURE shows an extraction process used to obtain extracts from each of the following plants (note that although the whole plant was used in the extract process for each of the Extracts to obtain the data in the Examples, plant parts are also contemplated and can be used by the process described in The FIGURE—e.g., stem, bark, root, flower, seed, fruit, leaf, sap etc.): *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense.*

DESCRIPTION OF ILLUSTRATIVE EMBODIMENTS

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin has been shown to have various drawbacks such as skin irritation and prolonged recovery periods.

The present invention is an effective alternative to the use of compositions and ingredients currently used to treat skin. As noted above, the inventors discovered various plant extracts (and combinations thereof) that can be used to treat skin conditions by, for example, inhibiting MMP-1, lipoxygenase, and/or tyrosinase activity in skin or by providing antioxidative protection to said skin. The following subsections provide information on the various extracts and plants that can be used, a method of identifying oily skin, and potential avenues for preparing corresponding product formulations. Therefore, these and other non-limiting aspects of the present invention are described in further detail below.

A. Plants and Extracts Thereof

The plants and extracts thereof of can be obtained by standard cultivation and extraction techniques known to those having ordinary skill in the art. Non-limiting examples of such techniques are provided below, in the Examples, and in The FIGURE. In addition, these extracts can be obtained through third parties such as Kunming Institute of Botany, Chinese Academy of Sciences, Yunnan, CHINA ("KIB") (e.g., the plant material used in the Examples was obtained from KIB.

For instance, a person of ordinary skill in the art would be able to isolate any one of the extracts identified below from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at $-20°$ C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-fluoro-carbon solvents), etc.

General information about the plants are provided below.

1. *Phaelous vulgaris*

The common bean, *Phaseolus vulgaris,* is an herbaceous annual plant domesticated independently in ancient Mesoamerica and the Andes, and now grown worldwide for its edible bean, popular both dry and as a green bean. The leaf is occasionally used as a leaf vegetable, and the straw is used for fodder. Botanically, the common bean is classified as a dicotyledon. Beans, squash and maize constituted the "Three Sisters" that provided the foundation of Native American agriculture. Beans are a legume and thus acquire their nitrogen through an association with rhizobia, a species of nitrogen-fixing bacteria. 18.3 million tonnes of dry common beans and 6.6 million tonnes of green beans were grown worldwide in 2007. The other major type of beans is broad beans (*Vicia faba*), of which only 3.7 million tonnes were grown in 2007. The commercial production of beans is well-distributed worldwide with countries in Asia, Africa, Europe, Oceania, South and North America all among the top bean growers. Brazil and India are the largest producers of dry beans while China produces, by far, the largest amount of green beans, almost as much as the rest of the top ten growers altogether.

The inventors have discovered that extracts of *Phaseolus vulgaris* have several biological activities, which can be beneficial to skin. The different portions of *Phaseolus vulgaris* can be used to obtain the corresponding extract. Non-limiting examples include its leaves, stems, bark, roots, fruit, flowers or flower buds, seeds, sap, and the entire plant.

2. *Citris sinensis*

An orange—specifically, the sweet orange—is the citrus *Citrus* x *sinensis* (syn. *Citrus aurantium* L. var. *dulcis* L., or *Citrus aurantium* Risso) and its fruit. The orange is a hybrid of ancient cultivated origin, possibly between pomelo (*Citrus maxima*) and mandarin (*Citrus reticulata*). It is a small flowering tree growing to about 10 m tall with evergreen leaves, which are arranged alternately, of ovate shape with crenulate margins and 4-10 cm long. The orange fruit is a hesperidium, a type of berry. Oranges originated in Southeast Asia. The fruit of *Citrus sinensis* is called sweet orange to distinguish it from *Citrus aurantium*, the bitter orange. The name is thought to ultimately derive from the Sanskrit for the orange tree, with its final form developing after passing through numerous intermediate languages. In a number of languages, it is known as a "Chinese apple" (e.g., Dutch Sinaasappel, "China's apple").

The inventors have discovered that extracts of *Citris sinensis* have several biological activities, which can be beneficial to skin. The different portions of *Citris sinensis* can be used to obtain the corresponding extract. Non-limiting examples include its leaves, stems, bark, roots, fruit, flowers or flower buds, seeds, sap, and the entire plant.

3. *Wedelia trilobata*

*Wedelia trilobata*, also known as yellow dots, rabbits paw, trailing daisy, creeping ox-eye, is part of the Family Asteraceae (aster family). A tropical perennial, with deepley lobed fleshy leaves, growing up to 10 inch tall, spreading like a mat, it makes a dense cover, if allowed. It blossoms profusely; the flowers are orange-yellow. Wedelia creeps and roots at the nodes. Wedelia is used to treat hepatitis, infections and to clear the placenta after birth. It grows in full sun/partial shade, moist well drained soil. It should be planted in frost free areas, and will be killed by frost but comes back in the spring. This plant type can be used as a ground cover.

The inventors have discovered that extracts of *Wedelia trilobata* have several biological activities, which can be beneficial to skin such as antioxidative properties. The different portions of *Wedelia trilobata* can be used to obtain the corresponding extract. Non-limiting examples include its leaves, stems, bark, roots, fruit, flowers or flower buds, seeds, sap, and the entire plant.

4. *Burretiodendron hsienmu*

*Burretiodendron hsienmu* is a species of flowering plant in the Tiliaceae family. It is found only in China. It is threatened by habitat loss. areas of Yunnan. Populations in Viet Nam represent a separate species. A slow-growing tree, it is found, sometimes as a dominant component, in lowland semi-deciduous woodland. Regeneration is observed to be strong in forest gaps. The timber is highly valued, and in many parts of its range mature trees have become very scarce or been eliminated. Habitat loss and degradation have also contributed to the decline.

The inventors have discovered that extracts of *Burretiodendron hsienmu* have several biological activities, which can be beneficial to skin. Non-limiting examples of some of these biological activities include antioxidant properties and the ability to inhibit MMP-1, lipoxygenase, and tyrosinase activity. All of the different portions of *Burretiodendron hsienmu* can be used to obtain the corresponding extract. Non-limiting examples include its leaves, stems, bark, roots, fruit, flowers or flower buds, seeds, sap, and the entire plant.

5. *Bauhinia brachycarpa* var. *cavaleriei*

*Bauhinia brachycarpa* var. *cavaleriei* is an evergreen plant. The leaves alternate, are simple, usually consisting of two lobes or almost bifoliolate with midrib between the two leaflets produced as a small spur. Flowers are showy, arranged in simple or panicled, terminal or axillary racemes. Hypanthium are sometimes long and cylindrical, sometimes short and turbinate. Calyx is entire or spathaceous, or cleft into two or five teeth. Petals number 5, slightly unequal, narrowed at the base into a claw, and are variously coloured. Stamens number between 5 and 10, filaments free or shortly connate, filiform, anthers versatile, dehiscing longitudinally. Ovary is seated on a stalk (gynophore), ovules many, style long or short and usually curved, stigma capitate, fruit a linear pod, dehiscent or indehiscent.

The inventors have discovered that extracts of *Bauhinia brachycarpa* var. *cavaleriei* have several biological activities, which can be beneficial to skin. Non-limiting examples of some of these biological activities include antioxidant properties and the ability to inhibit MMP-1, and lipoxygenase activity. All of the different portions of *Bauhinia brachycarpa* var. *cavaleriei* can be used to obtain the corresponding extract. Non-limiting examples include its leaves, stems, bark, roots, fruit, flowers or flower buds, seeds, sap, and the entire plant.

6. *Cystacanthus paniculatus*

*Cystacanthus paniculatus* is a shrub that can reach two meteres in height and is native to China. It is has green leaves and is capable of producing flowers.

The inventors have discovered that extracts of *Cystacanthus paniculatus* have several biological activities, which can be beneficial to skin. Non-limiting examples of some of these biological activities include antioxidant properties. All of the different portions of *Cystacanthus paniculatus* can be used to obtain the corresponding extract. Non-limiting examples include its leaves, stems, bark, roots, fruit, flowers or flower buds, seeds, sap, and the entire plant.

7. *Caesalpinia minax*

*Cyclosurus minax* is a plant that is native to China, Taiwan, India, Laos, Myanmar, Thailand, and Vietnam. It is capable of producing flowers and seeds.

The inventors have discovered that extracts of *Cyclosurus minax* have several biological activities, which can be beneficial to skin. All of the different portions of *Cyclosurus minax* can be used to obtain the corresponding extract. Non-limiting examples include its leaves, stems, bark, roots, fruit, flowers or flower buds, seeds, sap, and the entire plant.

8. *Pueraria wallichii*

*Pueraria wallichii* is a shrub that is native to China and is capable of producing flowers.

The inventors have discovered that extracts of *Pueraria wallichii* have several biological activities, which can be beneficial to skin. All of the different portions of *Pueraria wallichii* can be used to obtain the corresponding extract. Non-limiting examples include its leaves, stems, bark, roots, fruit, flowers or flower buds, seeds, sap, and the entire plant.d 9. *Tetracentron sinense*

*Tetracentron* is a genus of flowering plant, the sole living species being *Tetracentron sinense*. It was formerly considered the sole genus in the family Tetracentraceae, though modern botanists include it in the family Trochodendraceae together with the genus *Trochodendron*. It is native to southern China and the eastern Himalaya, where it grows at altitudes of 1100-3500 m in a temperate climate; it has no widely used common name in English, though is sometimes called "spur-leaf." It is a tree growing to 20-40 m tall. The leaves are deciduous (the Flora of China reporting it as evergreen is an error), borne singly at the apex of short spur shoots, each leaf dark green, broad heart-shaped, 5-13 cm long and 4-10 cm broad, with a rugose surface and a serrated margin. The spur shoots bear a one leaf each year, slowly lengthening with each subsequent year. The flowers are inconspicuous, yellowish green, without petals, produced on slender catkins 10-15 cm long; each flower is 1-2 mm diameter. The fruit is a follicle 2-5 mm diameter, containing 4-6 seeds. *Tetracentron* shares with *Trochodendron* the feature, very unusual in angiosperms, of lacking vessel elements in its wood. This has long been considered a very primitive character, resulting in the classification of these two genera in a basal position in the angiosperms; however, research in Molecular phylogenetics by the Angiosperm Phylogeny Group and others has shown that these two genera are not basal angiosperms, but basal eudicots. This suggests that the absence of vessel elements is a secondarily evolved character, not a primitive one.

The inventors have discovered that extracts of *Tetracentron sinense* have several biological activities, which can be beneficial to skin. Non-limiting examples of some of these biological activities include antioxidant properties and the ability to inhibit MMP-1 activity. All of the different portions of *Tetracentron sinense* can be used to obtain the corresponding extract. Non-limiting examples include its leaves, stems, bark, roots, fruit, flowers or flower buds, seeds, sap, and the entire plant.

10. *Bridelia insulana*

*Bridelia insulana*, also known as "maka ton," is a medium to large tree up to 25 m high, with glabrous branchlets, raised lenticels and very conspicuous on last generation branches. The bark is greyish. Stipules are very narrowly triangular, up to 5 by 0.8-1.3 mm, sparsely brownish puberulous, early caducous. Leaves have petioles 4-8 mm long and are glabrous; blade is broadly elliptic to obovate, 4.5-21 by 2.5-8.8 cm, with a length/width ratio 1.5-2. Flowers are staminate 2-2.5 mm in diameter, creamy yellow; pistillate ones are 2-3/3.5 mm in diameter, whitish cream with red disc; pedicel 0-1.5 mm long. Sepals are triangular, c. 1.2 by 1.2 mm, puberulous outside. Petals variable in shape, tiny, 0.3-0.5 by 0.3-0.5 mm, with a cuneate base.

The inventors have discovered that extracts of *Bridelia insulana* have several biological activities, which can be beneficial to skin. Non-limiting examples of some of these biological activities include antioxidant properties and the ability to inhibit MMP-1 activity. All of the different portions of *Bridelia insulana* can be used to obtain the corresponding extract. Non-limiting examples include its leaves, stems, bark, roots, fruit, flowers or flower buds, seeds, sap, and the entire plant.

11. *Hedyotis verticillata*

*Hedyotis verticillata*, locally known as Bongot (Mbo.), bosingau (Ilk.), manaal (Sub.), and salasik-lupa (Tag.). It is found in open places, old clearings, and thickets at a low altitude, from northern Luzon to Mindanao, in most islands and provinces. It also occurs in India to southern China and Malaya. This is a spreading, diffuse, branched herb, with branches 15 to 45 centimeters long. The leaves are stalkless, rough, rigid, slender, elliptic- or linear-lanceolate, 3.5 to 6 centimeters long, 2 to 5 millimeters wide, and pointed at both ends. The flowers are borne in clusters in the axils of the leaves. The calyx-teeth are triangular. The capsules are smooth, ovoid, and 2.5 to 3 millimeters long. According to sources, the plant is used for making poultices. These may be applied for headaches, and in the case of small children, upon the abdomen for stomachache. A decoction of the plant is drunk for dysentery.

The inventors have discovered that extracts of *Hedyotis verticillata* have several biological activities, which can be beneficial to skin. Non-limiting examples of some of these biological activities include antioxidant properties and the ability to inhibit MMP-1 activity. All of the different portions of *Hedyotis verticillata* can be used to obtain the corresponding extract. Non-limiting examples include its leaves, stems, bark, roots, fruit, flowers or flower buds, seeds, sap, and the entire plant.

12. *Syzygium fruiticosum*

*Syzygium fruticosum* is a 12 m tall tree, with dark brown branchlets when dry, compressed or grooved. Old branches are grayish white. Petioles are 1-1.5 cm; leaf blade are narrowly elliptic to elliptic, 9-13×3.5-5.5 cm, thinly leathery, abaxially reddish brown when dry, and adaxially brown and glossy when dry. Fruit is red when ripe, globose, 6-7 mm in diam., 1-seeded. Flowers in May-June. It grows in spare forests and wastelands from 500-1700 m in various Chinese provinces, Bangladesh, India, Mynamar and Thailand.

The inventors have discovered that extracts of *Syzygium fruiticosum* have several biological activities, which can be beneficial to skin. Non-limiting examples of some of these biological activities include antioxidant properties and the ability to inhibit MMP-1 activity. All of the different portions of *Syzygium fruiticosum* can be used to obtain the corresponding extract. Non-limiting examples include its leaves, stems, bark, roots, fruit, flowers or flower buds, seeds, sap, and the entire plant.

13. *Circidiphyllum japonicum*

*Cercidiphyllum japonicum* or Japanese Judas-tree is a species of flowering tree in the Cercidiphyllaceae family that commonly goes by the name Katsura tree. It is native to China and Japan. The tree is deciduous and grows to 40 to 60 feet. Its leaves are round. The tree flowers in March or April and produces winged seeds. There are several different cultivars grown including 'Aureum,' 'Heronswood Globe,' 'Pendula' and 'Ruby.'

The inventors have discovered that extracts of *Circidiphyllum japonicum* have several biological activities, which can be beneficial to skin. Non-limiting examples of some of these biological activities include antioxidant properties and the ability to inhibit MMP-1, and lipoxygenase activity. All of the different portions of *Circidiphyllum japonicum* can be used to obtain the corresponding extract. Non-limiting examples include its leaves, stems, bark, roots, fruit, flowers or flower buds, seeds, sap, and the entire plant.

14. *Bauhinia glauca*

*Bauhinia glauca* is a species of the genus *Bauhinia*, including more than 200 species of flowering plants in the subfamily Cæsalpinioideae of the large flowering plant family Fabaceae, with a pantropical distribution. The genus was named after the Bauhin brothers, Swiss-French botanists. Many species are widely planted in the tropics as "orchid trees," particularly in northern India, Vietnam and southeastern China. In the United States of America, the tree grows in Hawaii, coastal California, Texas, Louisiana, and Florida. *Bauhinia* trees typically reach a height of 6-12 m and their branches spread 3-6 m outwards. The lobed leaves usually are 10-15 cm across. The five-petaled flowers are 7.5-12.5 cm diameter, generally in shades of red, pink, purple, orange, or yellow, and are often fragrant. The tree begins flowering in late winter and often continues to flower into early summer. Depending on the species, Bauhinia flowers are usually in magenta, mauve, pink or white hues with crimson marking. It is know to produce flavonoids, which is pharmaceutically useful class of compounds.

The inventors have discovered that extracts of *Bauhinia glauca* have several biological activities, which can be beneficial to skin. Non-limiting examples of some of these biological activities include antioxidant properties and the ability to inhibit MMP-1, lipoxygenase, and tyrosinase activity. All of the different portions of *Bauhinia glauca* can be used to obtain the corresponding extract. Non-limiting examples include its leaves, stems, bark, roots, fruit, flowers or flower buds, seeds, sap, and the entire plant.

15. *Rhododendron siderophyllum*

*Rhododendron siderophyllum* is a 1-2 to 1-4 m tall shrub with brown young shoots that are densely scaly. Petioles are 5-15 mm and densely scaly; leaf blades are elliptic or elliptic-lanceolate, 3-7/11×1.2-3.5 cm; base is cuneate or rounded; apex is acuminate, acute or nearly obtuse; abaxial surface scales ae 0.5-2× their own diameter apart, or contiguous small to mid-sized, all similar or slightly unequal, brown and concave. It flowers in March-June, and grows in mixed forests, coniferous forests on slopes, and thickets at 1200/1800-3000 m, for example, in Guizhou, Sichuan, and Yunnan, China.

The inventors have discovered that extracts of *Rhododendron siderophyllum* have several biological activities, which can be beneficial to skin. Non-limiting examples of some of these biological activities include antioxidant properties and the ability to inhibit MMP-1, and lipoxygenase activity. All of the different portions of *Rhododendron siderophyllum* can be used to obtain the corresponding extract. Non-limiting examples include its leaves, stems, bark, roots, fruit, flowers or flower buds, seeds, sap, and the entire plant.

16. *Cudrania pubescens*

Is a viney plant that is native to China. It includes green leaves and is capable of producing flowers.

The inventors have discovered that extracts of *Cudrania pubescens* have several biological activities, which can be beneficial to skin. Non-limiting examples of some of these biological activities include antioxidant properties and the ability to inhibit lipoxygenase activity. All of the different portions of *Cudrania pubescens* can be used to obtain the corresponding extract. Non-limiting examples include its leaves, stems, bark, roots, fruit, flowers or flower buds, seeds, sap, and the entire plant.

17. *Cajanus cajan*

*Cajanus cajan*, the pigeon pea, is also known as toor dal (India), Congo pea or gungo pea (in Jamaica), gandule (in Puerto Rico), gunga pea, or no-eye pea. The cultivation of the pigeon pea goes back at least 3000 years, and today pigeon peas are widely cultivated in all tropical and semitropical regions of both the Old and the New World. Pigeon peas can be of a perennial variety, in which the crop can last 3-5 years (although the seed yield drops considerably after the first two years), or an annual variety more suitable for seed production. Being a legume, the pigeon pea enriches soil through symbiotic nitrogen fixation. Pigeon peas are in some areas an important crop for green manure, providing up to 40 kg nitrogen per hectare. The woody stems of pigeon peas can also be used as firewood, fencing and thatch.

The inventors have discovered that extracts of *Cajanus cajan* have several biological activities, which can be beneficial to skin. Non-limiting examples of some of these biological activities include antioxidant properties. All of the different portions of *Cajanus cajan* can be used to obtain the corresponding extract. Non-limiting examples include its leaves, stems, bark, roots, fruit, flowers or flower buds, seeds, sap, and the entire plant.

18. *Wendlandia uvariifolia*

*Wendlandia uvariifolia* is a small tree or shrud that can range in height from two to fifteen meters. It is native to China, and is capable of producing flowers.

The inventors have discovered that extracts of *Wendlandia uvariifolia* have several biological activities, which can be beneficial to skin. Non-limiting examples of some of these biological activities include antioxidant properties and the ability to inhibit MMP-1 and tyrosinase activity. All of the different portions of *Wendlandia uvariifolia* can be used to obtain the corresponding extract. Non-limiting examples include its leaves, stems, bark, roots, fruit, flowers or flower buds, seeds, sap, and the entire plant.

19. *Siegesbeckia glabrescens*

*Siegesbeckia glabrescens* has been used in traditional oriental medicine to treat cardiovascular diseases such as hypertension and angina pectoris, osteoporotic fractures, quadriplegia, paralysis, hemiplegia, and a constituent thereof (darutoside) has been shown to be an abortifacient in laboratory animals. It also is said to have anti-allergic activity, and may be a promising inhibitor of breast cancer cells.

The inventors have discovered that extracts of *Siegesbeckia glabrescens* have several biological activities, which can be beneficial to skin. All of the different portions of *Siegesbeckia glabrescens* can be used to obtain the corresponding extract. Non-limiting examples include its leaves, stems, bark, roots, fruit, flowers or flower buds, seeds, sap, and the entire plant.

20. *Azolla imbricata*

*Azolla imbricata* is a relatively common fern growing in Eastern Asia. It is aquatic and nitrogen fixing.

The inventors have discovered that extracts of *Azolla imbricata* have several biological activities, which can be beneficial to skin. All of the different portions of *Azolla imbricata* can be used to obtain the corresponding extract. Non-limiting examples include its leaves, stems, bark, roots, fruit, flowers or flower buds, seeds, sap, and the entire plant.

21. *Juncus bufonius*

*Juncus bufonius*, known commonly as toad rush, is a common species of rush found worldwide. It grows in moist and muddy places and is considered a weed in many areas. This is an annual monocot that is quite variable in appearance. It is sometimes described as a complex of variants labeled with one species name. It is generally a green clumping grasslike rush with many thin stems wrapped with few threadlike leaves. The flowers are borne in inflorescences and also in the joint where the inflorescence branches off of the stem. The flowering period is from September through March and is a grassy flower folded within tough bracts and sepals.

The inventors have discovered that extracts of *Juncus bufonius* have several biological activities, which can be beneficial to skin. Non-limiting examples of some of these biological activities include antioxidant properties. All of the different portions of *Juncus bufonius* can be used to obtain the corresponding extract. Non-limiting examples include its leaves, stems, bark, roots, fruit, flowers or flower buds, seeds, sap, and the entire plant.

22. *Poikilospermum suaveolens*

*Poikilospermum suaveolens*, also know as "blume," is widespread and found Indo-China, Southeastern China, Thailand, the Nicobar Islands, Peninsular Malaysia, Sumatra, Java, Borneo, Sulawesi, the Moluccas and the Philippines. It is an epiphytic, dioecious, evergreen stout and woody climber or scrambler. The leaf blade is broadly ovate to elliptical or obovate, measuring 10-40 cm×6-25 cm and usually hairless. The leaf base is wedge shaped to distinctly cordate and acute to obtuse at the apex. The flowers are in pseudo-umbellules. The male flower is sessile. There are (2-)4 tepals which are strongly incurved. There are (2-)4 stamens. The female flower is pedicellate with 4-lobed perianth. The stigma is with ligule. The one-seeded fruit is entirely covered by the persistent perianth. It is found up to 1500 m and prefers open forests and brushwoods.

The inventors have discovered that extracts of *Poikilospermum suaveolens* have several biological activities, which can be beneficial to skin. Non-limiting examples of some of these biological activities include antioxidant properties. All of the different portions of *Poikilospermum suaveolens* can be used to obtain the corresponding extract. Non-limiting examples include its leaves, stems, bark, roots, fruit, flowers or flower buds, seeds, sap, and the entire plant.

23. *Clerodendrum trichotomum* var.

*Clerodendrum trichotomum* is an upright, bushy, deciduous shrub or small tree from China and Japan with opposite, ovate, entire or sparsely toothed, dark green leaves to 20 cm (8 in) long. From late summer to mid-autumn it bears fragrant white flowers with red sepals in erect, axillary cymes to 20 cm across. The berries are bright blue. *Clerodendrum trichotomum* var. *fargesii* is from western China, and has young bronze leaves and flowers with green sepals. The flowers are followed by outstanding and eye-catching, metallic-blue berries in autumn. These berries are enclosed by colourful, maroon calyces (sepals of a flower).

The inventors have discovered that extracts of *Clerodendrum trichotomum* var. have several biological activities, which can be beneficial to skin. Non-limiting examples of some of these biological activities include antioxidant properties. All of the different portions of *Clerodendrum trichotomum* var. can be used to obtain the corresponding extract. Non-limiting examples include its leaves, stems, bark, roots, fruit, flowers or flower buds, seeds, sap, and the entire plant.

24. *Porandra ramosa*

*Porandra ramosa* is found in forests in west Guangxi, southwest Guizhou (Anlong Xian, Xingyi Xian), Yunnan, China at 400-2400 m. Its stems are up to 4 m, climbing, branched distally, and glabrous; internodes are 5-20 cm. Leaf sheaths are 2.5-6 cm and hirsute when young; petioles are 5-7 mm; leaf blades are elliptic to lanceolate, 8-16×2-4.5 cm, abaxially±hirsute, base-rounded to broadly cuneate, apex acuminate or caudate-acuminate. Heads contain several flowers; bracts are ovate-orbicular, ca. 3 mm. Sepals are oblong, carinate, 5-7 x ca. 3 mm, abaxially hirsute. Petals are pink, oblong, ca. 7 x ca. 3 mm. Filaments are ca. 7 mm; anthers are drip-shaped, ca. 2×1.5 mm. Ovaries are ca. 1 mm, hirsute. Seeds are 2 per valve, 3-4 mm. Flowers in April-August The inventors have discovered that extracts of *Porandra ramosa* have several biological activities, which can be beneficial to skin. All of the different portions of *Porandra ramosa* can be used to obtain the corresponding extract. Non-limiting examples include its leaves, stems, bark, roots, fruit, flowers or flower buds, seeds, sap, and the entire plant.

25. *Annona glabra*

*Annona glabra* is a tropical fruit tree in the family Annonaceae, in the same genus as the Soursop and Cherimoya. Common names include Pond-apple, Alligator-apple, Corkwood, Bobwood, and Monkey-apple. The name Alligator-apple derives from the fact that American Alligators sometimes eat the fruit. The tree is native to Florida in the United States, the Caribbean, Central and South America, and West Africa. It is common in the Everglades. It grows in swamps, is tolerant of saltwater, and cannot grow in dry soil. The trees grow to a height of around 10-12 m. They have thin, gray trunks and sometimes grow in clumps. The leaves are ovate to oblong with an acute tip, 8-15 cm long and 4-6 cm broad. The fruit is oblong to spherical and apple-sized or larger, 7-15 cm long and up to 9 cm diameter, and falls when it is green or ripening yellow. It disperses by floating to new locations, and it is food for many animal species. It is edible for humans, and can be made into jam, although the taste is usually not preferable to Soursop and other related fruits. The flesh is sweet-scented and agreeable in flavor, but it has never attained general popular use. It is a very troublesome invasive species in Australia. There it grows in estuaries and chokes mangrove swamps, where its seedlings carpet the banks and prevent other species from germinating or thriving. A recent study suggests that its alcoholic seed extract contains anticancer compounds that could be used pharmaceutically.

The inventors have discovered that extracts of *Annona glabra* have several biological activities, which can be beneficial to skin. All of the different portions of *Annona glabra* can be used to obtain the corresponding extract. Non-limiting examples include its leaves, stems, bark, roots, fruit, flowers or flower buds, seeds, sap, and the entire plant.

26. *Sterculia pexa*

*Sterculia pexa* is a trees with robust branchlets. Leaves are palmately compound; stipules are triangularly lanceolate, ca. 5 mm, pilose; petiole is usually 20-23 cm; leaflets number 7-9; leaflet blades are obovate-lanceolate or narrowly elliptic, 9-23×4-6 cm, abaxially densely stellate pubescent, adaxially nearly glabrous, lateral veins 22-44, parallel, base cuneate, margin entire, apex acuminate. Inflorescence is clustered at branchlet tips, racemose or paniculate, up to 20 cm. Epicalyx lobes are linear-lanceolate, ca. 1 cm. Calyx is white, campanulate, ca. 6 mm, divided to ½ length, abaxially densely stellate pubescent, lobes triangular, apex acuminate, incurved and apically coherent with each other. The male flower is androgynophore linear, glabrous. Anthers number 10-20 and are capitate. Female flower is ovary globose, 5-locular, densely puberulent. Follicle is brownish red, ellipsoid and slightly curved to sickle-shaped, 4-9×2-4 cm, 3-seeded, abaxially densely puberulent and hispid, adaxially stellate hairy, margin densely ciliate, apex obtuse. Seeds are black, oblong, ca. 1.5 cm. Flowers in October. The bark fiber is used for making rope or other similar purposes. The seeds are edible after boiling. The timber is good for furniture. It grows on sunny dry slopes, roadsides, cultivated around villages in southwest Guangxi, southern and southeastern Yunnan, China, as well as in Laos, Thailand, and Vietnam.

The inventors have discovered that extracts of *Sterculia pexa* have several biological activities, which can be beneficial to skin. All of the different portions of *Sterculia pexa* can be used to obtain the corresponding extract. Non-limiting examples include its leaves, stems, bark, roots, fruit, flowers or flower buds, seeds, sap, and the entire plant.

27. *Phoebe puwenensis*

*Phoebe puwenensis* is a large tree (up to 30 m) that grows in evergreen broad-leaved forests, usually at 880-1500 m in south Yunnan, China. Its bark is yellowish gray. Branchlets are robust, 5-6 mm in diam. at middle, densely yellowish brown tomentose, older ones with conspicuous leaf scars. Petioles are 1-2.5 cm, thick, densely yellowish brown or gray-black tomentose; leaf blade is obovate-elliptic or broadly obovate-lanceolate, 10-23×5-9 cm, abaxially densely yellowish brown villous, adaxially glabrous or with scattered appressed hairs or hairy along veins only. Panicles arise from middle and lower part of newly sprouted branchlet, 4.5-22(−25) cm, and are branched near the top of the peduncle, with yellowish brown tomentose. Pedicel is short, 2-3 mm, hairy. Flowers are yellowish, 4-5 mm. Perianth lobes are ovate, subequal, ca. 4 mm, apex acute, densely yellowish brown tomentose on both surfaces. Filaments are long white tomentose, those of 3rd series with sessile glands at base. Ovary is ovoid, upper part hairy; style slender; stigma dish-shaped. Fruit is ovoid, to 1.3 cmxca. 7 mm, glabrous; fruiting pedicel is not enlarged; persistent perianth lobes are leathery, clasping base of fruit. It floweres from March-April The inventors have discovered that extracts of *Phoebe puwenensis* have several biological activities, which can be beneficial to skin. Non-limiting examples of some of these biological activities include antioxidant properties and the ability to inhibit MMP-1 activity. All of the different portions of *Phoebe puwenensis* can be used to obtain the corresponding extract. Non-limiting examples include its leaves, stems, bark, roots, fruit, flowers or flower buds, seeds, sap, and the entire plant.

28. *Myriopteron extensum*

*Myriopteron extensum* has been shown to produce several natural products of medicinal interest, including steroidal saponins and flavanones. It grows as a liana of 10 m in height. Branchlets are pale gray, lenticellate, glabrous. Petiole is 1.5-4 cm; leaf blade is ovate-elliptic to broadly ovate, 8-18(−30)×4-11(−22) cm, membranous, glabrous to sparsely pilose; lateral veins number 7-9 pairs. Pedicel is threadlike, 5-10 mm. Sepals are ca. 1×0.7 mm, ovate, obtuse, delicate, glabrous or ciliate, reflexed at anthesis. Corolla is ca. 3 mm in diam., glabrous; lobes are lanceolate or ovate-oblong. Corona lobes are 3-4 mm, glabrous. Follicles are 7-7.5×3-3.5 cm, with ca. 20 wings. Flowers in May-August. It grows in thickets and open woods at 600-1600 m. in Guangxi, Guizhou, and Yunnan, China, as well as in India, Indonesia, Laos, Myanmar, Thailand and Vietnam. The roots are used as medicine for pulmonary tuberculosis and cough.

The inventors have discovered that extracts of *Myriopteron extensum* have several biological activities, which can be beneficial to skin. Non-limiting examples of some of these biological activities include antioxidant properties. All of the different portions of *Myriopteron extensum* can be used to obtain the corresponding extract. Non-limiting examples include its leaves, stems, bark, roots, fruit, flowers or flower buds, seeds, sap, and the entire plant.

29. *Croton lachnocarpa*

*Croton lachnocarpa* is a shrub that can reach one to three meters in height. It is native to China and is capable of producing fruits and flowers.

The inventors have discovered that extracts of *Croton lachnocarpa* have several biological activities, which can be beneficial to skin. Non-limiting examples of some of these biological activities include antioxidant properties and the ability to inhibit MMP-1 activity. All of the different portions of *Croton lachnocarpa* can be used to obtain the corresponding extract. Non-limiting examples include its leaves, stems, bark, roots, fruit, flowers or flower buds, seeds, sap, and the entire plant.

30. *Dillenia turbinata*

*Dillenia turbinata* is an evergreen tree about 30 m tall. It has stout branchlets stout. Petioles are 2-6 cm, narrowly winged; leaf blade are obovate to long obovate. Racemes are terminal, 3-5-flowered; peduncle is 3-5 cm, stout, both bracts and bractlets are absent. Its flowers number 2-7, fragrant, 10-12 cm in diam., 4-5 cm in diam. in bud. Sepals are oval, 2.5-4.5×2-3 cm, thickly fleshy, unequal, with outer ones larger than inner ones. Petals are yellow, yellowish white, or reddish, obovate, 5-7 cm, thin, narrow based with rounded apexes. Stamens are in 2 distinct groups, outer very numerous, slightly curved in bud, 1.5-2 cm, inner ca. 25, reflexed in bud; anthers are dehiscing with pores. It flowers in April-May. It grows in mixed evergreen forests, wet places in valleys; 700-1000 m. S. Guangxi, Hainan, and S. Yunnan, China, as well as Vietnam.

The inventors have discovered that extracts of *Dillenia turbinata* have several biological activities, which can be beneficial to skin. Non-limiting examples of some of these biological activities include antioxidant properties and the ability to inhibit MMP-1 activity. All of the different portions of *Dillenia turbinata* can be used to obtain the corresponding extract. Non-limiting examples include its leaves, stems, bark, roots, fruit, flowers or flower buds, seeds, sap, and the entire plant.

31. *Alpinia blepharocalyx*

*Alpinia blepharocalyx* grows in dense or sparse forests at 400-1200 m. in Guangdong, Guangxi, and Yunnan, China, as well as Bangladesh, India, Laos, Myanmar, Thailand, and Vietnam. Pseudostems are 1-3 m. Ligules are about. 6 mm, with villous apex; leaf blades are adaxially dark green, abaxially pale green, lanceolate or oblanceolate, base is attenuate, apex is acuminate, mucronate. Racemes are drooping. Flowering occurs in March-July The inventors have discovered that extracts of *Alpinia blepharocalyx* have several biological activities, which can be beneficial to skin. Non-limiting examples of some of these biological activities include antioxidant properties. All of the different portions of *Alpinia blepharocalyx* can be used to obtain the corresponding extract. Non-limiting examples include its leaves, stems, bark, roots, fruit, flowers or flower buds, seeds, sap, and the entire plant.

32. *Crotalaria spectabilis*

*Crotalaria spectabilis*, also known as "showy rattlebox," is an annual semiwoody herb in temperate areas, and a short-lived shrub in its frost-free subtropical and tropical range. In Puerto Rico, it grows up to 2 m in height and 3.5 cm in basal diameter. It normally has a single stem. The lower stems are covered with whorled, short, shelf-like old leaf bases and stipule remnants. The leaves and fruiting branches are shed progressively upward after they mature so that foliage and branches are only found on the upper portion of the stem. The mid- and lower stem has a white, brittle, medium-hard wood with a 1.5-mm pith. The upper stem, branches, and foliage are green to yellow-green. The plant is supported by a tap and lateral system of stiff, tan roots. The simple, whorled leaves are oblanceolate to elliptic, 5 to 17 cm long, entire, and have a 2-mm petiole and broad, triangular stipules. The inflorescences are terminal or sub-terminal racemes with 20 to 25 flowers with linear-triangular bracts. The bright yellow unequal flowers are 1.5 to 2 cm long. Inflated brown to black legumes are 3 to 5 cm long and 1.8 to 2 cm thick. They contain several hard, shiny brown to black seeds 4.5 mm long (author's observation, Damron and Jacob 2001. Howard 1988, Liogier 1988, Stevens and others 2001). Showy rattlebox is native to the Indo-Malaysia area (Parrotta 2001). It has been planted widely and has naturalized in many tropical countries including the Southern United States, Hawaii, and Puerto Rico (International Legume Database and Information Service 2002).

The inventors have discovered that extracts of *Crotalaria spectabilis* have several biological activities, which can be beneficial to skin. Non-limiting examples of some of these biological activities include antioxidant properties. All of the different portions of *Crotalaria spectabilis* can be used to obtain the corresponding extract. Non-limiting examples include its leaves, stems, bark, roots, fruit, flowers or flower buds, seeds, sap, and the entire plant.

33. *Ficus lacor*

*Ficus lacor*, also known as the "pakur tree," is deciduous and is native to northern China. It is known for its diaphoretic medicinal properties.

The inventors have discovered that extracts of *Ficus lacor* have several biological activities, which can be beneficial to skin. Non-limiting examples of some of these biological activities include antioxidant properties and the ability to inhibit MMP-1 activity. All of the different portions of *Ficus lacor* can be used to obtain the corresponding extract. Non-limiting examples include its leaves, stems, bark, roots, fruit, flowers or flower buds, seeds, sap, and the entire plant.

34. *Ravenala madagascariensis*

*Ravenala madagascariensis*, commonly known as Traveller's Tree or Traveller's Palm, is a species of plant from Madagascar. It is not a true palm (family Arecaceae), but a member of the bird-of-paradise family, Strelitziaceae. *R. madagascariensis* is the sole member of its genus, and is closely related to the southern African genus *Strelitzia* and the South American genus *Phenakospermum*. Some older classifications include these genera in the banana family (Musaceae). It has been given the name "Traveller's palm" because the sheaths of the stems hold rainwater, which can be used as an emergency drinking supply. The enormous paddle-shaped leaves are borne on long petioles, in a distinctive fan shape aligned in a single plane. The large white flowers are structurally similar to those of its relatives, the bird-of-paradise flowers *Strelitzia reginae* and *Strelitzia nicolai*, but less attractive. In tropical and subtropical regions, the plant is widely cultivated for its distinctive habit and foliage. Ruffed lemurs are a known pollinator of this plant, and given the size and structure of the inflorescences, as well as the lemur's selectivity, method of feeding, and long muzzle, this relationship is thought to have co-evolved. The color of the palm varies slightly from the tip of the leaves which are green, to the end of the leaf stem which is yellow. It has a trunk which emerges as it matures. During its early years the trunk is underneath the ground, but as the palm grows older, it loses some of its fan-like leaves and reveals a brown rigid trunk.

The inventors have discovered that extracts of *Ravenala madagascariensis* have several biological activities, which can be beneficial to skin. Non-limiting examples of some of these biological activities include antioxidant properties and the ability to inhibit MMP-1 activity. All of the different portions of *Ravenala madagascariensis* can be used to obtain the corresponding extract. Non-limiting examples include its leaves, stems, bark, roots, fruit, flowers or flower buds, seeds, sap, and the entire plant.

35. *Cocculus orbiculatus*

*Cocculus orbiculatus*, also know as queen coralbead, is indigenous to Hawaii. It is a partially woody, sprawling shrub/vine. It is less than two feet in height but can be quite sprawling due to its vine-like nature. It is used as an accent and ground cover, as well as on fences and trellises. It lives longer than five years, and produces non-showy flowers of white and yellow. It is susceptible to insects, such as aphids and ants. If grows well in dry environments with full or partial sun. It was used by early Hawaiians to bind parts of grass dwellings.

The inventors have discovered that extracts of *Cocculus orbiculatus* have several biological activities, which can be beneficial to skin. Non-limiting examples of some of these biological activities include antioxidant properties. All of the different portions of *Cocculus orbiculatus* can be used to obtain the corresponding extract. Non-limiting examples include its leaves, stems, bark, roots, fruit, flowers or flower buds, seeds, sap, and the entire plant.

36. *Drynaria fortunei*

*Drynaria fortunei*, is a medicinal fern, also known as "Gu-Sui-Bu." It is used to strength bone, and to treat deficiency syndrome of the kidney marked by back pain, tinnitus, impairment of hearing and looseness of teeth, traumatic injury, bone fracture, as well as external use for alopecia areata and vitiligo.

The inventors have discovered that extracts of *Drynaria fortunei* have several biological activities, which can be beneficial to skin. All of the different portions of *Drynaria fortunei* can be used to obtain the corresponding extract. Non-limiting examples include its leaves, stems, bark, roots, fruit, flowers or flower buds, seeds, sap, and the entire plant.

37. *Acrachne racemosa*

*Acrachne racemosa* is a terrestrial annual. Its stems are erect or ascending, geniculate, decumbent, or lax, sometimes rooting at nodes, caespitose, tufted, or clustered, terete, round in cross section, or polygonal, with stem internodes hollow. Stems with inflorescence are less than 1 m tall. Leaves are mostly cauline, conspicuously 2-ranked, distichous, with sheathing at base. The leaf sheath is mostly open, or loose, smooth, glabrous, blade keeled, with leaf sheath and blade differentiated. Leaf blades are linear, 2-10 mm wide, mostly flat, mostly glabrous, more or less hairy. A ligule is present, fringed, ciliate, or lobed membrane. Inflorescence is terminal, with 2 or more spikes, fascicles, glomerules, heads, or clusters per culm. Inflorescence is a panicle with narrowly racemose or spicate branches, digitately arranged spicate branches, 2-10 branches, to more than 10. Inflorescence branches are 1-sided, lower panicle branches are whorled, rachis is angular, flowers are bisexual, spikelets sessile or subsessile, laterally compressed, less than 3 mm wide, with 3-40 florets, solitary or paired at rachis nodes, all alike and fertile, bisexual, disarticulating above the glumes, glumes persistent, disarticulating beneath or between the florets, secund, in rows on one side of rachis. Rachilla or pedicel is glabrous, glumes are present, with empty bracts.

The inventors have discovered that extracts of *Acrachne racemosa* have several biological activities, which can be beneficial to skin. All of the different portions of *Acrachne racemosa* can be used to obtain the corresponding extract. Non-limiting examples include its leaves, stems, bark, roots, fruit, flowers or flower buds, seeds, sap, and the entire plant.

38. *Pseuderanthemum polyanthum*

*Pseuderanthemum polyanthum* is an herb that is native to China and India. It is capable of producing white to purplish colored flowers.

The inventors have discovered that extracts of *Pseuder-anthemum polyanthum* have several biological activities, which can be beneficial to skin. Non-limiting examples of some of these biological activities include antioxidant properties. All of the different portions of *Pseuderanthemum polyanthum* can be used to obtain the corresponding extract. Non-limiting examples include its leaves, stems, bark, roots, fruit, flowers or flower buds, seeds, sap, and the entire plant.

39. *Eriobotrys serrata*

*Eriobotry serrata* is a 10-20 m tall tree. Branchlets are yellowish brown, stout, densely tomentose when young, glabrescent. Stipules are caducous, not seen; petiole is 1.5-3 cm, glabrous; leaf blade is obovate or oblanceolate, 9-23× 3.5-13 cm, leathery, adaxially lustrous, midvein is prominent on both surfaces, lateral veins number 10-16 pairs, glabrous or abaxially sparsely brown pubescent along veins, base is attenuate, margin is incurved-serrate; apex is obtuse or acute. Panicle is about 8 cm in diameter, many flowered; peduncle is densely yellow tomentose; bracts are not seen. Pedicel is 2-3 mm, densely yellow tomentose. Flowers are 8-10 mm in diam. Hypanthium is cupular, 3-4 mm, abaxially densely yellow tomentose. Sepals are ovate, 2-2.5 cm, abaxially yellow tomentose, apex is obtuse or acute. Petals are white, obovate, 3-3.5 mm. Stamens number 20. Ovary is pubescent apically, (2 or) 3- or 4 (or 5)-loculed, with 2 ovules per locule; styles (2 or) 3 or 4 (or 5), base is pubescent. Pome is green, globose or pyriform, 1.5-1.8 cm in diam., subglabrous; sepals are reflexed.

The inventors have discovered that extracts of *Eriobotrys serrata* have several biological activities, which can be beneficial to skin. Non-limiting examples of some of these biological activities include antioxidant properties and the ability to inhibit MMP-1 activity. All of the different portions of *Eriobotrys serrata* can be used to obtain the corresponding extract. Non-limiting examples include its leaves, stems, bark, roots, fruit, flowers or flower buds, seeds, sap, and the entire plant.

40. *Veronia arborea*

*Veronia arborea*, or "Tree *Vernonia*" is a medium sized tree, growing up to 15 m tall. Bark is brown or blackish. Young branchlets are cylindrical and velvety. Alternately spirally arranged leaves are clustered at the ends of branchlets. Leaf stalk is 0.6-2.6 cm long, velvety. Leaf blade is 8.5-19 cm long, 4-11 cm wide, generally elliptic or slightly obovate. Tip is pointed or abruptly ending into a point, and the base is wedge-shaped. Margin is entire or sometimes distantly double toothed. Leaves are velvety on the underside. Pinkish purple flower-heads are borne in large panicled cymes, at the end of branches. Fruit is dry, ribbed, 1-seeded. Tree *Vernonia* is found along margins of evergreen forests, up to 1900 m, in South and Central Sahyadris in Western Ghats and parts of Northeast India. Aqueous and methanol leaf extracts promote wound-healing activity significantly in a number of wound models. High rate of wound contraction, decrease in the period for epithelialisation, high skin breaking strength and granulation strength, increase in dry granulation tissue weight, elevated hydroxyproline content and increased collagenation in histopathological section were observed in animals treated with methanol leaf extract and aqueous leaf extract when compared to the control group of animals.

The inventors have discovered that extracts of *Veronia arborea* have several biological activities, which can be beneficial to skin. Non-limiting examples of some of these biological activities include antioxidant properties. All of the different portions of *Veronia arborea* can be used to obtain the corresponding extract. Non-limiting examples include its leaves, stems, bark, roots, fruit, flowers or flower buds, seeds, sap, and the entire plant.

41. *Adianthum caudatum*

*Adiantum caudatum* is a particularly vigorous fern known as walking maidenhair fern. Although it emerges late after a hard winter, these plants have survived 7° F., to form a 5' wide patch in 5 years. The 1.5" wide×2' long arching fronds, which emerge pink in spring, root into the ground at the tips forming a new plant. Moist soils result in faster growth, but plants are quite happy in a fairly dry, sandy soil.

The inventors have discovered that extracts of *Adianthum caudatum* have several biological activities, which can be beneficial to skin. All of the different portions of *Adianthum caudatum* can be used to obtain the corresponding extract. Non-limiting examples include its leaves, stems, bark, roots, fruit, flowers or flower buds, seeds, sap, and the entire plant.

42. *Phaseolus lunatus*

*Phaseolus lunatus* is a legume. It is grown for its seed, which is eaten as a vegetable. It is commonly known as the lima bean or butter bean; it is also known as Haba bean, Pallar bean, Burma bean, Guffin bean, Hibbert bean, Sieva bean, Rangoon bean, Madagascar bean, Paiga, Paigya, prolific bean, civet bean, or sugar bean. The *P. lunatus* is of Andean and Mesoamerican origin. Two separate domestication events are believed to have occurred. The first, taking place in the Andes around 2000 BC, produced a large-seeded variety (Lima type), while the second, taking place most likely in Mesoamerica around AD 800, produced a small-seeded variety (Sieva type). By 1301, cultivation had spread to North America, and in the sixteenth century the plant arrived and began to be cultivated in the Eastern Hemisphere. The small-seeded wild form (Sieva type) is found distributed from Mexico to Argentina, generally below 1600 meters above sea level, while the large-seeded wild form (Lima type) is found distributed in the north of Peru, between 320 and 2030 meters above sea level. The term butter bean is widely utilized for a large, flat and white variety of lima bean (*P. lunatus* var. *macrocarpus*, or *P. limensis*). In the Southern United States the Sieva type are traditionally called butter beans, also otherwise known as the Dixie or Henderson type. In that area, lima beans and butter beans are seen as two distinct types of beans. In the United Kingdom, "butter beans" refer to either dried beans which can be purchased to re-hydrate or the canned variety which are ready to use. In culinary use, lima beans and butter beans are distinctly different, the former being small and green, the latter large and yellow. In areas where both are considered to be lima beans, the green variety may be labeled as "baby" (and less commonly "junior") limas.

The inventors have discovered that extracts of *Phaseolus lunatus* have several biological activities, which can be beneficial to skin. Non-limiting examples of some of these biological activities include antioxidant properties. All of the different portions of *Phaseolus lunatus* can be used to obtain the corresponding extract. Non-limiting examples include its leaves, stems, bark, roots, fruit, flowers or flower buds, seeds, sap, and the entire plant.

43. *Ipomoea cairica*

*Ipomoea cairica* morning glory has many common names, including Mile-a-minute Vine, Messina Creeper, Cairo Morning Glory, Coast Morning Glory and Railroad Creeper. This vining perennial has palmate leaves and large, showy white to lavender flowers. Each fruit matures at about 1 cm across and contains hairy seeds. Its native range is uncertain, though it is believed to originate from a rather wide area, ranging from Cape Verde to the Arabian Peninsula, including northern Africa. Because of human dispersal, it occurs today on most continents as an introduced species and is sometimes a noxious weed. It is a major problem along the coast of New South Wales. In the United States it occurs in Hawaii, California, all the gulf coast states, as well as Arkansas and Missouri. Some plant nurseries sell this plant as an ornamental.

The inventors have discovered that extracts of *Ipomoea cairica* have several biological activities, which can be beneficial to skin. Non-limiting examples of some of these biological activities include antioxidant properties. All of the different portions of *Ipomoea cairica* can be used to obtain the corresponding extract. Non-limiting examples include its leaves, stems, bark, roots, fruit, flowers or flower buds, seeds, sap, and the entire plant.

44. *Alopecurus aequalis*

*Alopecurus aequalis* is a common species of grass known by the common name shortawn foxtail. It is native to much of the temperate Northern Hemisphere from Eurasia to North America, where it can be found in many types of habitat. This perennial bunchgrass is variable in appearance. It produces bunches of erect stems between 10 and about 70 centimeters in height. The leaves are short, rarely exceeding 10 centimeters long. The cylindrical inflorescence is a few centimeters long and blooms with white to yellow to bright orange anthers.

The inventors have discovered that extracts of *Alopecurus aequalis* have several biological activities, which can be beneficial to skin. Non-limiting examples of some of these biological activities include antioxidant properties. All of the different portions of *Alopecurus aequalis* can be used to obtain the corresponding extract. Non-limiting examples include its leaves, stems, bark, roots, fruit, flowers or flower buds, seeds, sap, and the entire plant.

45. *Arenga pinnata*

*Arenga pinnata* (syn. *Arenga saccharifera*) is an economically important feather palm native to tropical Asia, from eastern India east to Malaysia, Indonesia, and the Philippines in the east. Common names include Sugar Palm, Arenga Palm, Areng palm, Black-fiber palm, Gomuti Palm, Aren, Enau, Irok, and Kaong. It is a medium-sized palm, growing to 20 m tall, with the trunk remaining covered by the rough old leaf bases. The leaves are 6-12 m long and 1.5 m broad, pinnate, with the pinnae in 1-6 rows, 40-70 cm long and 5 cm broad. The fruit is subglobose, 7 cm diameter, green maturing black. It is not a threatened species, though it is locally rare in some parts of its range. It serves as an important part of the diet of several endangered species, including cloud rats of the genus *Phloeomys*.

The inventors have discovered that extracts of *Arenga pinnata* have several biological activities, which can be beneficial to skin. Non-limiting examples of some of these biological activities include antioxidant properties and the ability to inhibit MMP-1 activity. All of the different portions of *Arenga pinnata* can be used to obtain the corresponding extract. Non-limiting examples include its leaves, stems, bark, roots, fruit, flowers or flower buds, seeds, sap, and the entire plant.

46. *Rhynchosia yunnanensis*

*Rhynchosia yunnanensis* grows as vine, herbaceous or sometimes almost woody, around 50 cm. Stems are slightly robust, densely villous or tomentose, with dark brown sessile glands. Leaves are pinnately 3-foliolate; stipules are lanceolate, 4-8 mm, usually persistent; petiole is 2.5-6 cm; stipels are absent; petiolules are 1-3 mm and hairy; leaflets are papery; terminal leaflet is reniform or oblate, 2-3.7×2.5-5.3 cm, densely gray villous, with dark brown glands, basal veins number 3, lateral veins number 2-4 pairs, reticulate veins are visible, base is shallowly cordate to almost truncate, margin is slightly sinuate, slightly reflexed when dried, apex is rounded or almost truncate, usually with small mucro; lateral leaflets are smaller, slightly oblique. Raceme is axillary, rarely solitary or branched, 2-5 cm; peduncle is 1-3.5 cm, densely hairy; bracts are lanceolate, 4-7 mm, persistent. Flowers are yellow, 1.4-2 cm; pedicel is 2-8 mm. Calyx is 5-lobed; lobes lanceolate, longer than tube, lower one longest; standard subcircular or obovate-circular, 1-1.5 cm, glabrous, base with 2 auricles; wings elliptic to obovate-elliptic, 7-13 mm, auriculate on one side; keel is very wide, subobovate, 7-14 mm, without auricle. Ovary is densely silky hairy, sessile; ovules number 1 or 2; the style is linear, with lower part silky hairy. Legume is reddish brown, obovate-orbicular to ellipsoid, 2-2.5×0.7-0.8 cm, sparsely pubescent, with apex beaked. Seeds are dark brown, reniform or orbicular, 4-5×5-6 mm.

The inventors have discovered that extracts of *Rhynchosia yunnanensis* have several biological activities, which can be beneficial to skin. Non-limiting examples of some of these biological activities include antioxidant properties. All of the different portions of *Rhynchosia yunnanensis* can be used to obtain the corresponding extract. Non-limiting examples include its leaves, stems, bark, roots, fruit, flowers or flower buds, seeds, sap, and the entire plant.

47. *Syzygium* cumini

Jambul (*Syzygium cumini*) is an evergreen tropical tree in the flowering plant family Myrtaceae, native to Bangladesh, India, Nepal, Pakistan and Indonesia. The word 'Jambul' is sometimes mistranslated as 'Blackberry', which is a different fruit. It is also known as Jaam/Kalojaam, Jamun, Nerale Hannu, Naval pazham, Neredupandu, Jamblang, Jambolan, Jambula, Black Plum, Damson Plum, Duhat Plum, Jambolan Plum, Java Plum or Portuguese Plum. "Malabar plum" may also refer to other species of *Syzygium*. Historically, the tree was exclusive to the Indian Sub-continent, and so widespread across the region that one of the old names of India (or the Indian region) is Jambu-Dvipa (literally: the island of jambul fruit). It is now also grown in other areas of southern and southeastern Asia including the Philippines, Myanmar, and Afghanistan. The tree was also introduced to Florida, USA in 1911 by the USDA, and is also now commonly grown in Suriname and Trinidad and Tobago. In Brazil, where it was introduced from India during Portuguese colonization, it has dispersed spontaneously in the wild in some places, as its fruits are eagerly sought by various native birds such as thrushes, tanagers and the Great Kiskadee. Scientific synonyms include *Syzygium jambolanum, Eugenia cumini* and *Eugenia jambolana*.

The inventors have discovered that extracts of *Syzygium cumini* have several biological activities, which can be beneficial to skin. Non-limiting examples of some of these biological activities include antioxidant properties and the ability to inhibit MMP-1 activity. All of the different portions of *Syzygium cumini* can be used to obtain the corresponding extract. Non-limiting examples include its leaves, stems, bark, roots, fruit, flowers or flower buds, seeds, sap, and the entire plant.

48. *Clausena dunniana*

*Cyclosurus minax Clausena dunniana* are trees 2-5 m tall, and they are deciduous. The leaves are 5-15 and foliolate; petiolules are 4-8 mm; leaflet blades are ovate to lanceolate, 4-10 x 2-5 cm, glabrous or villous, base asymmetric, margin serrate or rarely repand, apex acute to acuminate. Inflorescences terminal. Flowers 4 (or 5)-merous, globose in bud. Stamens are 8 (or 10); filaments *geniculate* at middle, subulate at apex. The disk is small. The ovary is globose;

style shorter than ovary. Fruit is bluish black when ripe, globose, and 1-1.5 cm in diameter, 1- or 2-seeded. It exists is Montane forests, moist areas in mountains, at 300-1500 m. Locations include Guangdong, Guangxi, Guizhou, W Hubei, Hunan, E and SE Sichuan, S Yunnan [NE Vietnam].

The inventors have discovered that extracts of *Clausena dunniana* have several biological activities, which can be beneficial to skin. All of the different portions of *Clausena dunniana* can be used to obtain the corresponding extract. Non-limiting examples include its leaves, stems, bark, roots, fruit, flowers or flower buds, seeds, sap, and the entire plant.

49. *Cyclosurus parasiticus*

*Cyclosurus parasiticus* is a fern that is native to Hong Kong and China.

The inventors have discovered that extracts of *Cyclosurus parasiticus* have several biological activities, which can be beneficial to skin. Non-limiting examples of some of these biological activities include the ability to inhibit MMP-1 activity. All of the different portions of *Cyclosurus parasiticus* can be used to obtain the corresponding extract. Non-limiting examples include its leaves, stems, bark, roots, fruit, flowers or flower buds, seeds, sap, and the entire plant.

50. *Solanum carolinense*

Carolina Horsenettle (*Solanum carolinense*) is not a true nettle, but a member of the Solanaceae, or nightshade family. It is a perennial herbaceous plant, native to southeastern United States that has spread widely throughout North America. This plant has hard spines along the stems that can penetrate the skin and break off, causing much pain. Though there are other horsenettle nightshades, *S. carolinense* is the species most widely known simply as "the horsenettle." It is also known as Radical Weed or Sand Brier (or "briar"), while more ambiguous names are "bull nettle," "tread-softly" and "apple of Sodom."

The inventors have discovered that extracts of *Solanum carolinense* have several biological activities, which can be beneficial to skin. Non-limiting examples of some of these biological activities include antioxidant properties. All of the different portions of *Solanum carolinense* can be used to obtain the corresponding extract. Non-limiting examples include its leaves, stems, bark, roots, fruit, flowers or flower buds, seeds, sap, and the entire plant.

B. Extraction Methods

In addition to the extraction process described in The FIGURE, a person of ordinary skill in the art would be able to isolate any one of the extracts identified above from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-fluoro-carbon solvents), etc.

C. Determination of Oily Skin

Oily skin tends to present itself as having a shiny, thick, and dull appearance. It typically feels oily and usually has coarse pores and pimples and other unsightly blemishes due to overproduction of sebum from sebaceous glands and from clogged/blocked pores. As such, oily skin usually has oil producing sebaceous glands that are overactive and produce more oil than is needed. The oil oozes and gives the skin a greasy shine. The pores are enlarged and the skin has a coarse look.

D. Compositions of the Present Invention

1. Combinations and Amounts of Ingredients

It is contemplated that the compositions of the present invention can include any one of *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus*, and/or *Solanum carolinense*, or any combination thereof, or all of such plants, plant parts, or extracts thereof, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50 of such plants, plant parts, or extracts thereof. The compositions can also include additional ingredients described throughout this specification. The concentrations of the plant extracts and/or additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the plant extracts identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the plant extracts and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. Nos. 6,387,398; 6,203,802; 5,411,744; Kreuter 1988).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection (e.g., an injectable solution), and oral administration and formulation (e.g., tablets, capsules, etc.).

3. Products

The compositions of the present invention can be incorporated into products. Non-limiting examples of products include cosmetic products, food-based products (e.g., fortified water, energy drinks, nutritional drinks, vitamins, supplements, solid foods), pharmaceutical products, etc. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2008), 12$^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, Ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) water-proofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Sunscreen Agents

UV absorption agents that can be used in combination with the compositions of the present invention include chemical and physical sunblocks. Non-limiting examples of chemical sunblocks that can be used include para-amino-benzoic acid (PABA), PABA esters (glyceryl PABA, amyldimethyl PABA and octyldimethyl PABA), butyl PABA, ethyl PABA, ethyl dihydroxypropyl PABA, benzo-phenones (oxybenzone, sulisobenzone, benzophenone, and benzophenone-1 through 12), cinnamates (octyl methoxy-cinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycin-namate), cinnamate esters, salicylates (homomethyl salicy-late, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl ami-nobenzoate, lawsone with dihydroxyacetone, ethylhexyl tri-azone, dioctyl butamido triazone, benzylidene malonate polysiloxane, terephthalylidene dicamphor sulfonic acid, disodium phenyl dibenzimidazole tetrasulfonate, diethyl-amino hydroxybenzoyl hexyl benzoate, bis di ethyl amino hydroxybenzoyl benzoate, bis benzoxazoylphenyl ethylhex-ylimino triazine, drometrizole trisiloxane, methylene bis-benzotriazolyl tetramethylbutyiphenol, and bis-ethylhexy-loxyphenol methoxyphenyltriazine, 4-methylbenzylidenecamphor, and isopentyl 4-methoxycin-namate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

ii. Moisturizing Agents

Non-limiting examples of moisturizing agents that can be used with the compositions of the present invention include amino acids, chondroitin sulfate, diglycerin, erythritol, fruc-tose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone car-boxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspoly-mer, acrylates copolymer, alanine, algae extract, aloe bar-badensis, aloe-barbadensis extract, aloe barbadensis gel, althea *officinalis* extract, aluminum starch octenylsuccinate, aluminum stearate, apricot (*prunus armeniaca*) kernel oil, arginine, arginine aspartate, *arnica montana* extract, ascor-bic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*Borago officinalis*) extract, 2-bromo-2-nitropropane-1,3-diol, butcherbroom (*ruscus aculeatus*) extract, butylene glycol, *Calendula offi-cinalis* extract, *Calendula officinalis* oil, candelilla (*euphor-bia* cerifera) wax, canola oil, caprylic/capric triglyceride, cardamon (*Elettaria cardamomum*) oil, carnauba (*Coperni-cia cerifera*) wax, carrageenan (*Chondrus crispus*), carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystear-ate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexaca-prate, DMDM hydantoin, DNA, erythritol, ethoxydiglycol, ethyl linoleate, eucalyptus globulus oil, evening primrose (*Oenothera biennis*) oil, fatty acids, tructose, gelatin, gera-nium maculatum oil, glucosamine, glucose glutamate, glu-tamic acid, glycereth-26, glycerin, glycerol, glyceryl dis-tearate, glyceryl hydroxystearate, glyceryl laurate, glyceryl linoleate, glyceryl myristate, glyceryl oleate, glyceryl stear-ate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avel-lana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydro-lyzed elastin, hydrolyzed glycosaminoglycans, hydrolyzed keratin, hydrolyzed soy protein, hydroxylated lanolin, hydroxyproline, imidazolidinyl urea, iodopropynyl butylcar-bamate, isocetyl stearate, isocetyl stearoyl stearate, isodecyl oleate, isopropyl isostearate, isopropyl lanolate, isopropyl myristate, isopropyl palmitate, isopropyl stearate, isostear-amide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lav-ender (*Lavandula angustifolia*) oil, lecithin, lemon (*Citrus medica limonum*) oil, linoleic acid, linolenic acid, macada-mia *ternifolia* nut oil, magnesium stearate, magnesium sul-fate, maltitol, matricaria (*Chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydrox-ystearate, octyl palmitate, octyl salicylate, octyl stearate, oleic acid, olive (*Olea europaea*) oil, orange (citrus *Auran-*

*tium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*salvia officinalis*) oil, salicylic acid, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

iii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

iv. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

v. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

vi. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

vii. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

viii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949;

2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

A. Example 1 (Materials and Methods for Obtaining Extracts)

The extracts identified in Table 1 were prepared from the whole plant. Each plant was individually obtained, ground, and dried, to produce a powder. The powder was treated according to the process described in The FIGURE. Each extract in Table 1 was prepared by and provided to the inventors by Kunming Institute of Botany, Chinese Academy of Sciences, Yunnan, CHINA.

B. Example 2 (Efficacy of Extracts)

Each extract prepared according to the process described in Example 1 was subjected to a variety of assays to determine their skin efficacy (note the H$_2$O part (v) extract was used for testing—see The FIGURE). The following Table 1 provides a summary of these data. A description of the assays used to obtain these data is provided below Table 1.

TABLE 1*

| Plant Extract** | AO Activity | MMP-1 | Lipoxygenase | Tyrosinase Inhibition |
|---|---|---|---|---|
| Phaseolus vulgaris | | | | |
| Citrus sinensis | | | | |
| Wedelia trilobata | EFFECT | | | |

TABLE 1*-continued

| Plant Extract** | AO Activity | MMP-1 | Lipoxygenase | Tyrosinase Inhibition |
|---|---|---|---|---|
| Burretiodendron hsienmu | EFFECT | EFFECT | EFFECT | EFFECT |
| Bauhinia brachycarpa var. cavaleriei | EFFECT | EFFECT | EFFECT | |
| Cystancanthus paniculatus | EFFECT | | | |
| Caesalpinia minax | | | | |
| Pueraria wallichii | | | | |
| Tetracentron sinense | EFFECT | EFFECT | | |
| Bridelia insulana | EFFECT | EFFECT | | |
| Hedyotis verticillata | EFFECT | EFFECT | | |
| Syzygium fruticosum | EFFECT | EFFECT | | |
| Circidiphyllum japonicum | EFFECT | EFFECT | EFFECT | |
| Bauhinia glauca | EFFECT | EFFECT | EFFECT | EFFECT |
| Rhododendron siderophyllum | EFFECT | EFFECT | EFFECT | |
| Cudrania pubescens | EFFECT | | EFFECT | |
| Cajanus cajan | EFFECT | | | |
| Wendlandia uvariifolia | EFFECT | EFFECT | | EFFECT |
| Siegesbeckia glabrescens | | | | |
| Azolla imbricata | | | | |
| Juncus bufonius | EFFECT | | | |
| Poikilospermum suaveolens | EFFECT | | | |
| Clerodendrum trichotomum var. fargesii | EFFECT | | | |
| Porandra ramosa | | | | |
| Annona glabra | | | | |
| Sterculia pexa | | | | |
| Phoebe puwenensis | EFFECT | EFFECT | | |
| Myriopteron extensum | EFFECT | | | |
| Croton lachnocarpa | EFFECT | EFFECT | | |
| Dillenia turbinata | EFFECT | EFFECT | | |
| Alpinia blepharocalyx | EFFECT | | | |
| Crotalaria spectabilis | EFFECT | | | |
| Ficus lacor | EFFECT | EFFECT | | |
| Ravenala madagascariensis | EFFECT | EFFECT | | |
| Cocculus orbiculatus | EFFECT | | | |
| Drynaria fortunei | | | | |
| Acrachne racemosa | | | | |
| Pseuderanthemum poylanthum | EFFECT | | | |
| Eriobotrys serrata | EFFECT | EFFECT | | |
| Vernonia arborea | EFFECT | | | |
| Adianthum caudatum | | | | |
| Phaseolus lunatus | EFFECT | | | |
| Ipomoea cairica | EFFECT | | | |
| Alopecurus aequalis | EFFECT | | | |
| Arenga pinnata | EFFECT | EFFECT | | |
| Rhynchosia yunnanensis | EFFECT | | | |
| Syzygium cumini | EFFECT | EFFECT | | |
| Clausena dunniana | | | | |
| Cyclosurus parasiticus | | | EFFECT | |
| Solanum carolinense | EFFECT | | | |

*"EFFECT" means that the given extract had a measurable effect on the corresponding activity being assayed, which is indicative of beneficial results when applied to skin.
**In addition to the extracts identified in Table 1, these data suggest that any number of different combinations of such extracts can be used in a product to produce a multi-functional product. Alternatively, the extracts can be used individually, which still can result in a product having multiple benefits.

Antioxidant (AO) assay: An in vitro bioassay that measures the total anti-oxidant capacity of an extract. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents.

Anti-Oxidant capacity kit #709001 from Cayman Chemical (Ann Arbor, Michigan USA) was used as an in vitro bioassay to measure the total anti-oxidant capacity of each of the extracts identified in Table 1. The protocol was followed according to manufacturer recommendations. The assay relied on antioxidants in the sample to inhibit the oxidation of ABTS® (2,2'-azino-di-[3-ethylbenzthiazoline sulphonate]) to ABTS®.+ by metmyoglobin. The capacity of the antioxidants in the sample to prevent ABTS oxidation was compared with that Trolox, a water-soluble tocopherol analogue, and was quantified as a molar Trolox equivalent.

Matrix Metalloproteinase Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen was used as an in vitro assay to measure MMP1 enzymatic activity for each of the extracts identified in Tables 1-3. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid.

The Colorimetric LO Inhibitor screening kit (#760700, Cayman Chemical) was used to determine the ability of each of the extracts identified in Tables 1-3 to inhibit enzyme activity. Purified 15-lipoxygenase and test extracts were mixed in assay buffer and incubated with shaking for 10 min at room temperature. Following incubation, arachidonic acid was added to initiate the reaction and mixtures incubated for an additional 10 min at room temperature. Colorimetric substrate was added to terminate catalysis and color progression was evaluated by fluorescence plate reading at 490 nm. The percent inhibition of lipoxyganse activity was calculated compared to non-treated controls to determine the ability of test extracts to inhibit the activity of purified enzyme.

Tyrosinase Activity Assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes.

Purified mushroom tyrosinase (Sigma) was incubated with its substrate L-Dopa (Fisher) in the presence or absence of each of the extracts in Table 1. Pigment formation was evaluated by colorimetric plate reading at 490 nm. The percent inhibition of mushroom tyrosinase activity was calculated compared to non-treated controls to determine the ability of test extracts to inhibit the activity of purified enzyme. Test extract inhibition was compared with that of kojic acid (Sigma).

C. Example 3 (Particular Combinations of Extracts)

Based, in part, on the above data, it was discovered that a combination of an aqueous extract from the whole plant of *Burretiodendron hsienmu*, an aqueous extract from the whole plant of *Bauhinia brachycarpa* var. *cavaleriei*, and an aqueous extract from the whole plant of *Tetracentron sinense* can be used to inhibit/reduce the activity of MMP-1 in skin cells. This can lead to increased collagen within skin, which can reduce the appearance of fine lines and wrinkles. Aqueous extracts of the whole plant were used to obtain this data (see The FIGURE, H2O part (v)). This combination can also be used to inhibit/reduce lipoxygenase activity, tyrosinase activity, and protect skin cells from oxidative damage caused by free-radicals and reactive oxygen species. The use of whole plant can lead to an extract having different ingredients when compared with an extract from a portion of the same plant (e.g., leaf or flower extract).

A further discovery was the combination of an aqueous extract from the whole plant of *Circidiphyllum japonicum*, an aqueous extract from the whole plant of *Bauhinia glauca*, and an aqueous extract from the whole plant of *Rhododendron siderophyllum* to inhibit/reduce lipoxygenase activity in said skin. This can be useful in reducing sebum production in skin, which can lead to an effective way to control or reduce the appearance of oily or shiny skin. This combination can also inhibit MMP-1 activity, tyrosinase activity, and protect skin cells from oxidative damage caused by free-radicals and reactive oxygen species. As previously noted, aqueous extracts of the whole plant were used to obtain this data (see The FIGURE, H2O part (v)). The use of whole plant can lead to an extract having different ingredients when compared, with an extract from a portion of the same plant (e.g., leaf or flower extract).

An additional discovery was the combination of an aqueous extract from the whole plant of *Burretiodendron hsienmu*, an aqueous extract from the whole plant of *Bauhinia glauca*, and an aqueous extract from the whole plant of *Wendlandia uvariifolia* to reduce/inhibit tyrosinase activity in skin cells. By attacking the tyrosinase pathway, a reduction in melanin production can be obtained. This allows for the skin to appear lighter, thus reducing the appearance of hyperpigmented skin (e.g., dark spots, liver spots, age spots, sun spots, and melasmic skin). This combination can also inhibit MMP-1 activity, lipoxygenase activity, and protect skin cells from oxidative damage caused by free-radicals and reactive oxygen species. As previously noted, aqueous extracts of the whole plant were used to obtain this data (see The FIGURE, H2O part (v)). Again, the use of whole plant can lead to an extract having different ingredients when compared, with an extract from a portion of the same plant (e.g., leaf or flower extract).

D. Example 4 (Testing Vehicles and Sample Compositions)

Tables 2 and 3 describe generic skin testing formulations in which a skin active ingredient can be incorporated into to determine the types of skin benefits that can be attributed to the skin active ingredient. These formulations are prepared in such a manner that any resulting skin benefit from topical application of the formula to skin can be directly attributed to the skin active ingredient being tested. In the context of the present invention, the skin active ingredient that can be tested can be a plant, plant part, or extract thereof from *Phaseolus vulgaris, Citris sinensis, Wedelia trilobata, Burretiodendron hsienmu, Bauhinia brachycarpa* var. *cavaleriei, Cystacanthus paniculatus, Caesalpinia minax, Pueraria wallichii, Tetracentron sinense, Bridelia insulana, Hedyotis verticillata, Syzygium fruticosum, Cercidiphyllum japonicum, Bauhinia glauca, Rhododendron siderophyllum, Cudrania pubescens, Cajanus cajan, Wendlandia uvariifolia, Siegesbeckia glabrescens, Azolla imbricate, Juncus bufonius, Poikilospermum suaveolens, Clerodendrum trichotomum* var. *fargesii, Porandra ramosa, Annona glabra, Sterculia pexa, Phoebe puwenensis, Myriopteron extensum, Croton lachnocarpa, Dillenia turbinata, Alpinia blepharocalyx, Crotalaria spectabilis, Ficus lacor, Ravenala madagascariensis, Cocculus orbiculatus, Drynaria fortunei, Acrachne racemosa, Pseuderanthemum polyanthum, Eriobotrys serrata, Vernonia arborea, Adianthum caudatum, Phaseolus lunatus, Ipomoea cairica, Alopecurus aequalis, Arenga pinnata, Rhynchosia yunnanensis, Syzygium cumini, Clausena dunniana, Cyclosurus parasiticus,* and/or *Solanum carolinense,* or any combination thereof, or all of such plants, plant parts, or extracts thereof, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50 of such plants, plant parts, or extracts thereof. Any portion of the plant extract can be used for testing (e.g., root, stem, leaf, flower, flower bulb, bark, fruit, sap, whole plant etc.). It should be recognized that other standard testing vehicles can also be used to determine the skin benefit properties of extracts obtained from the plant extracts and that the following formulations are non-limiting testing vehicles.

TABLE 2*

| Ingredient | % Concentration (by weight) |
|---|---|
| Phase A | |
| Water | 84.80 |
| Xanthum gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |

50

TABLE 2*-continued

| Ingredient | % Concentration (by weight) |
|---|---|
| Phase C | |
| Plant Extract | 2.0 |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.

TABLE 3*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Plant Extract** | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.

The formulations represented in Table 4-9 are non-limiting examples of the types of formulations that can be prepared in the context of the present invention. Any standard method can be used to prepare such formulations. For instance, simple mixing of the ingredients in a beaker can be used. One should mix such ingredients and add heat as necessary to obtain a homogenous composition.

Table 4 includes a non-limiting example of a composition of the present invention. The composition can be formulated into an emulsion (e.g., o/w, w/o, o/w/o, w/o/w, etc.) and the additional ingredients identified throughout the specification can be included into the Table 4 composition (e.g., by adjusting the water content of composition). Further, the concentration ranges of the ingredients identified in Table 6 can vary depending on a desired formulation (e.g., cream, lotion, moisturizer cleanser, etc.).

TABLE 4

| Ingredient | % Concentration (by weight) |
|---|---|
| Water | q.s. |
| Plant Extract* | 0.1% to 10% |
| Glycerin | 3 to 40% |

TABLE 4-continued

| Ingredient | % Concentration (by weight) |
| --- | --- |
| Butylene glycol | 0.0001 to 10% |
| Propylene glycol | 0.0001 to 10% |
| Phenoxyethanol | 0.0001 to 10% |
| Disodium EDTA | 0.0001 to 10% |
| Steareth-20 | 0.0001 to 10% |
| Chlorhexidine Diglunonate | 0.0001 to 10% |
| Potasium Sorbate | 0.0001 to 10% |
| Preservative* | 0.0001 to 2% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.
**Any preservative can be used identified in the specification or those known in the art.

Table 5 includes a non-limiting example of a composition of the present invention. The composition can be formulated into an emulsion (e.g., o/w, w/o, o/w/o, w/o/w, etc.) and the additional ingredients identified throughout the specification can be included into the Table 5 composition (e.g., by adjusting the water content of composition). Further, the concentration ranges of the ingredients identified in Table 5 can vary depending on a desired formulation (e.g., cream, lotion, moisturizer cleanser, etc.).

TABLE 5

| Ingredient | % Concentration (by weight) |
| --- | --- |
| Water | q.s. |
| Plant Extract* | 0.1% to 10% |
| Dimethicone | 0.0001 to 10% |
| Triethanolamine | 0.0001 to 10% |
| Phenonip | 0.0001 to 10% |
| Betaine | 0.0001 to 10% |
| Disodium EDTA | 0.0001 to 10% |
| Tocopheryl acetate | 0.0001 to 10% |
| Prodew 400 | 0.0001 to 10% |
| Preservative** | 0.0001 to 2% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.
**Any preservative can be used identified in the specification or those known in the art.

Table 6 includes a non-limiting example of a composition of the present invention. The composition can be formulated into an emulsion (e.g., o/w, w/o, o/w/o, w/o/w, etc.) and the additional ingredients identified throughout the specification can be included into the Table 6 composition (e.g., by adjusting the water content of composition). Further, the concentration ranges of the ingredients identified in Table 6 can vary depending on a desired formulation (e.g., cream, lotion, moisturizer cleanser, etc.). In particular embodiments, the Table 8 composition can be a moisturizer.

TABLE 6

| Ingredient | % Concentration (by weight) |
| --- | --- |
| Water | q.s. |
| Plant Extract* | 0.1% to 10% |
| Glycerin | 0.0001 to 10% |
| Pentylene Glycol | 0.0001 to 10% |

TABLE 6-continued

| Ingredient | % Concentration (by weight) |
| --- | --- |
| Capryl Glycol | 0.0001 to 10% |
| Disodium EDTA | 0.0001 to 10% |
| Capric/Caprylic Triglyceride | 0.0001 to 10% |
| Lipex 205 (Shea Butter) | 0.0001 to 10% |
| Squalane | 0.0001 to 10% |
| Cetyl Alcohol | 0.0001 to 10% |
| Dimethicone | 0.0001 to 10% |
| Ceramide II | 0.0001 to 10% |
| Stearic Acid | 0.0001 to 10% |
| Super Sterol Ester | 0.0001 to 10% |
| Arlacel 165 | 0.0001 to 10% |
| Simulgel 600 | 0.0001 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.

Table 7 includes a non-limiting example of a composition of the present invention. The composition can be formulated into an emulsion (e.g., o/w, w/o, o/w/o, w/o/w, etc.) and the additional ingredients identified throughout the specification can be included into the Table 7 composition (e.g., by adjusting the water content of composition). Further, the concentration ranges of the ingredients identified in Table 7 can vary depending on a desired formulation (e.g., cream, lotion, moisturizer cleanser, etc.). In particular embodiments, the Table 9 composition can be a moisturizer.

TABLE 7

| Ingredient | % Concentration (by weight) |
| --- | --- |
| Water | q.s. |
| Plant Extract* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Petrolatum | 0.0001 to 10% |
| Squalane | 0.0001 to 10% |
| Cetyl Alcohol | 0.0001 to 10% |
| Arlacel 165 | 0.0001 to 10% |
| Dimethicone | 0.0001 to 10% |
| Simulgel 600 | 0.0001 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.

Table 8 includes a non-limiting example of a composition of the present invention. The composition can be formulated into an emulsion (e.g., o/w, w/o, o/w/o, w/o/w, etc.) and the additional ingredients identified throughout the specification can be included into the Table 8 composition (e.g., by adjusting the water content of composition). Further, the concentration ranges of the ingredients identified in Table 8 can vary depending on a desired formulation (e.g., cream, lotion, moisturizer cleanser, etc.). In particular embodiments, the Table 8 composition can be a sunscreen lotion.

TABLE 8

| Ingredient | % Concentration (by weight) |
|---|---|
| Water | q.s. |
| Plant Extract* | 0.1% to 10% |
| Xanthan Gum | 0.0001 to 10% |
| Disodium EDTA | 0.0001 to 10% |
| Pentylene Glycol | 0.0001 to 10% |
| Capryl Glycol | 0.0001 to 10% |
| Pemulen TR-1 | 0.0001 to 10% |
| Triethanolamine | 0.0001 to 10% |
| PVP/Hexadecene Copolymer | 0.0001 to 10% |
| Finsolv TN | 10 to 30% |
| Sorbitan Isostearate | 0.0001 to 10% |
| Sunscreen Ingredient** | 2 to 25% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.).
**Sunscreen ingredient can be any sunscreen ingredient, or combination of such ingredients, identified in the specification or known to those of ordinary skill in the art. In one embodiment, the sunscreen ingredient is a combination of zinc oxide and titanium dioxide. For instance, each of the combinations noted in Example 3 can be used.

Table 9 includes a non-limiting example of a composition of the present invention. The additional ingredients identified throughout the specification can be included into the Table 9 composition (e.g., by adjusting the water content of composition). Further, the concentration ranges of the ingredients identified in Table 9 can vary depending on a desired formulation (e.g., cream, lotion, moisturizer cleanser, etc.). In particular embodiments, the Table 9 composition can be a cleanser.

TABLE 9

| Ingredient | % Concentration (by weight) |
|---|---|
| Water | q.s. |
| Plant Extract* | 0.1% to 10% |
| Disodium EDTA | 0.0001 to 10% |
| Citric Acid | 0.0001 to 10% |
| Pentylene Glycol | 0.0001 to 10% |
| Capryl Glycol | 0.0001 to 10% |
| sodium methyl cocoyl taurate | 10 to 30% |
| sodium cocoamphodiacetate | 1 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. Any portion of the plant can be used to create the skin-active extract (e.g., root, stem, leaf, flower, flower bulb, bark, fruit, seed, seed pod, sap, whole plant etc.). For instance, each of the combinations noted in Example 3 can be used.

E. Example 5 (Assays that can be Used to Test Compositions)

The efficacy of compositions comprising the plant extracts identified throughout the specification, or a combination of such extracts (including, for example, the formulations identified in Tables 2-9), can be determined by methods known to those of ordinary skill in the art. The following are non-limiting assays that can be used in the context of the present invention. It should be recognized that other testing procedures can be used, including, for example, objective and subjective procedures.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a formula containing any one, or any combination thereof, of the extracts identified throughout the specification. Repeat measurements are taken at regular intervals to determine the formula's ability to reduce redness, inflammation, or skin irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the area of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay: Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-0C2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7).

B16 Melanogenesis Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$, and treated with each of the extracts identified in the specification. Following incubation, melanin secretion can be measured by absorbance at 405 nm and cellular viability can be quantified.

Collagen Stimulation Assay: Collagen is an extracellular matrix protein critical for skin structure. Increased synthesis of collagen helps improve skin firmness and elasticity. This bioassay analyzes the effect of extracts on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples are pipetted into the wells and any procollagen peptide □present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color develops in proportion to the amount of procollagen peptide bound in the initial step using a microplate reader for detection at 450 nm. The color development is stopped and the intensity of the color is measured.

In particular, the assay could be performed as follows: subconfluent normal human adult epidermal fibroblasts (Cascade Biologics) cultivated in standard DMEM growth medium with 10% fetal bovine serum (Mediatech) at 37° C. in 10% $CO_2$, can be treated with each of the extracts identified in the specification. Following incubation, cell culture medium can be collected and the amount of procollagen peptide secretion can be quantified using a sandwich enzyme linked immuno-sorbant assay (ELISA) from Takara (#MK101).

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method for treating skin of a person in need thereof, the method comprising topically applying to the skin of the person a composition comprising an effective amount of an aqueous, alcoholic, or aqueous-alcoholic extract from *Ficus*

*lacor*, wherein the extract from *Ficus lacor* reduces oxidation in the skin or reduces MMP-1 activity in the skin, wherein the skin of the person comprises a fine line or wrinkle, wherein the composition is topically applied to the fine line or wrinkle, and wherein the composition treats the fine line or wrinkle.

2. The method of claim 1, wherein the composition increases the firmness of the skin.

3. The method of claim 1, wherein the skin of the person further comprises oily skin, and wherein the composition is further applied to the oily skin.

4. The method of claim 3, wherein the oily skin has coarse pores, red spots, pustules, pimples, whiteheads, or blackheads.

5. The method of claim 3, wherein the composition reduces sebum production.

6. The method of claim 1, wherein the skin of the person further comprises dark spots, melasma, hyperpigmentation, or uneven skin tone, and wherein the composition is further applied to the skin having dark spots, melasma, hyperpigmentation, or uneven skin tone.

7. The method of claim 6, wherein the composition reduces dark spots, melasma, hyperpigmentation, or uneven skin tone.

8. The method of claim 1, wherein the extract from *Ficus lacor* reduces oxidation in the skin.

9. The method of claim 1, wherein the extract from *Ficus lacor* reduces MMP-1 activity in the skin.

10. The method of claim 1, wherein the extract from *Ficus lacor* reduces oxidation in the skin and reduces MMP-1 activity in the skin.

11. The method of claim 1, wherein the composition is an emulsion.

12. The method of claim 11, wherein the composition is an oil-in-water emulsion.

13. The method of claim 1, wherein the composition is a cream or a lotion.

14. The method of claim 1, wherein the composition is a solution.

15. The method of claim 1, wherein the composition is a gel.

16. The method of claim 1, wherein the composition is anhydrous.

17. The method of claim 1, wherein the composition comprises 0.001% to 5%, by weight, of the extract.

18. The method of claim 1, wherein the composition further comprises sesame oil and/or vetiver oil.

19. The method of claim 1, wherein the composition further comprises:
   (a) water;
   (b) a chelating agent;
   (c) a moisturizing agent;
   (d) a preservative; and
   (e) a thickening agent.

20. The method of claim 1, wherein the extract is a lyophilized extract in powdered form.

21. The method of claim 1, wherein the extract is from the whole plant of *Ficus lacor.*

22. The method of claim 1, wherein the extract is an alcoholic extract.

* * * * *